United States Patent
Kemp et al.

(10) Patent No.: US 9,596,993 B2
(45) Date of Patent: Mar. 21, 2017

(54) AUTOMATIC CALIBRATION SYSTEMS AND METHODS OF USE

(75) Inventors: Nathaniel J. Kemp, Concord, MA (US); Elizabeth Begin, Billerica, MA (US); Badr Elmaanaoui, Billerica, MA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/402,798

(22) Filed: Feb. 22, 2012

(65) Prior Publication Data

US 2012/0224751 A1  Sep. 6, 2012

Related U.S. Application Data

(63) Continuation-in-part of application No. 13/243,399, filed on Sep. 23, 2011, now Pat. No. 8,593,641, which is a continuation of application No. 12/172,980, filed on Jul. 14, 2008, now Pat. No. 8,049,900.

(60) Provisional application No. 60/949,467, filed on Jul. 12, 2007.

(51) Int. Cl.
| | |
|---|---|
| *G06K 9/62* | (2006.01) |
| *A61B 5/00* | (2006.01) |
| *G01B 9/02* | (2006.01) |
| *G01M 11/00* | (2006.01) |
| *G01N 21/47* | (2006.01) |
| *G01N 21/27* | (2006.01) |

(52) U.S. Cl.
CPC .......... *A61B 5/0073* (2013.01); *A61B 5/0066* (2013.01); *A61B 5/0084* (2013.01); *A61B 5/6852* (2013.01); *G01B 9/02004* (2013.01); *G01B 9/02057* (2013.01); *G01B 9/02069* (2013.01); *G01B 9/02083* (2013.01); *G01B 9/02091* (2013.01); *G01M 11/31* (2013.01); *G01N 21/4795* (2013.01); *A61B 5/7257* (2013.01); *G01B 2290/25* (2013.01); *G01N 21/274* (2013.01)

(58) Field of Classification Search
CPC .. A61B 5/6852; A61B 5/0066; A61B 5/02156
USPC .................. 356/479, 497; 382/128, 254, 275
See application file for complete search history.

(56) References Cited

U.S. PATENT DOCUMENTS

| | | |
|---|---|---|
| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |

(Continued)

FOREIGN PATENT DOCUMENTS

| | | |
|---|---|---|
| EP | 1041373 A2 | 10/2000 |
| EP | 01172637 A1 | 1/2002 |

(Continued)

OTHER PUBLICATIONS

International Search Report and Written Opinion for Application No. PCT/US2013/26834, mailed Apr. 24, 2013.

(Continued)

*Primary Examiner* — Kara E Geisel
*Assistant Examiner* — Dominic J Bologna

(57) ABSTRACT

The disclosed automatic calibration systems and methods provide a repeatable way to detect internal catheter reflections and to shift the internal catheter reflections to calibrate an image.

3 Claims, 23 Drawing Sheets

(56) References Cited

U.S. PATENT DOCUMENTS

| | | | |
|---|---|---|---|
| 4,050,450 A * | 9/1977 | Polanyi | A61B 5/1459 |
| | | | 356/243.5 |
| 4,140,364 A | 2/1979 | Yamashita et al. | |
| 4,274,423 A | 6/1981 | Mizuno et al. | |
| 4,344,438 A | 8/1982 | Schultz | |
| 4,398,791 A | 8/1983 | Dorsey | |
| 4,432,370 A | 2/1984 | Hughes et al. | |
| 4,552,554 A | 11/1985 | Gould et al. | |
| 4,577,543 A | 3/1986 | Wilson | |
| 4,676,980 A | 6/1987 | Segal et al. | |
| 4,682,895 A | 7/1987 | Costello | |
| 4,733,665 A | 3/1988 | Palmaz | |
| 4,744,619 A | 5/1988 | Cameron | |
| 4,762,129 A | 8/1988 | Bonzel | |
| 4,766,386 A | 8/1988 | Oliver et al. | |
| 4,771,774 A | 9/1988 | Simpson et al. | |
| 4,794,931 A | 1/1989 | Yock | |
| 4,800,886 A | 1/1989 | Nestor | |
| 4,803,639 A | 2/1989 | Steele et al. | |
| 4,816,567 A | 3/1989 | Cabilly et al. | |
| 4,819,740 A | 4/1989 | Warrington | |
| 4,821,731 A | 4/1989 | Martinelli et al. | |
| 4,824,435 A | 4/1989 | Giesy et al. | |
| 4,830,023 A | 5/1989 | de Toledo et al. | |
| 4,834,093 A | 5/1989 | Littleford et al. | |
| 4,841,977 A | 6/1989 | Griffith et al. | |
| 4,864,578 A | 9/1989 | Proffitt et al. | |
| 4,873,690 A | 10/1989 | Adams | |
| 4,877,314 A | 10/1989 | Kanamori | |
| 4,887,606 A | 12/1989 | Yock et al. | |
| 4,917,085 A | 4/1990 | Smith | |
| 4,917,097 A | 4/1990 | Proudian et al. | |
| 4,928,693 A | 5/1990 | Goodin et al. | |
| 4,932,413 A | 6/1990 | Shockey et al. | |
| 4,932,419 A | 6/1990 | de Toledo | |
| 4,948,229 A | 8/1990 | Soref | |
| 4,951,677 A | 8/1990 | Crowley et al. | |
| 4,969,742 A | 11/1990 | Falk et al. | |
| 4,987,412 A | 1/1991 | Vaitekunas et al. | |
| 4,993,412 A | 2/1991 | Murphy-Chutorian | |
| 4,998,972 A | 3/1991 | Chin et al. | |
| 5,000,185 A | 3/1991 | Yock | |
| 5,024,234 A | 6/1991 | Leary et al. | |
| 5,025,445 A | 6/1991 | Anderson et al. | |
| 5,032,123 A | 7/1991 | Katz et al. | |
| 5,037,169 A | 8/1991 | Chun | |
| 5,039,193 A | 8/1991 | Snow et al. | |
| 5,040,548 A | 8/1991 | Yock | |
| 5,041,108 A | 8/1991 | Fox et al. | |
| 5,054,492 A | 10/1991 | Scribner et al. | |
| 5,065,010 A | 11/1991 | Knute | |
| 5,065,769 A | 11/1991 | de Toledo | |
| 5,085,221 A | 2/1992 | Ingebrigtsen et al. | |
| 5,095,911 A | 3/1992 | Pomeranz | |
| 5,100,424 A | 3/1992 | Jang et al. | |
| 5,120,308 A | 6/1992 | Hess | |
| 5,125,137 A | 6/1992 | Corl et al. | |
| 5,135,486 A | 8/1992 | Eberle et al. | |
| 5,135,516 A | 8/1992 | Sahatjian et al. | |
| 5,155,439 A | 10/1992 | Holmbo et al. | |
| 5,158,548 A | 10/1992 | Lau et al. | |
| 5,163,445 A | 11/1992 | Christian et al. | |
| 5,167,233 A | 12/1992 | Eberle et al. | |
| 5,174,295 A | 12/1992 | Christian et al. | |
| 5,176,141 A | 1/1993 | Bom et al. | |
| 5,176,674 A | 1/1993 | Hofmann | |
| 5,178,159 A | 1/1993 | Christian | |
| 5,183,048 A | 2/1993 | Eberle | |
| 5,188,632 A | 2/1993 | Goldenberg | |
| 5,201,316 A | 4/1993 | Pomeranz et al. | |
| 5,202,745 A | 4/1993 | Sorin et al. | |
| 5,203,779 A | 4/1993 | Muller et al. | |
| 5,220,922 A | 6/1993 | Barany | |
| 5,224,953 A | 7/1993 | Morgentaler | |
| 5,226,421 A | 7/1993 | Frisbie et al. | |
| 5,240,003 A | 8/1993 | Lancee et al. | |
| 5,240,437 A | 8/1993 | Christian | |
| 5,242,460 A | 9/1993 | Klein et al. | |
| 5,243,988 A | 9/1993 | Sieben et al. | |
| 5,257,974 A | 11/1993 | Cox | |
| 5,266,302 A | 11/1993 | Peyman et al. | |
| 5,267,954 A | 12/1993 | Nita | |
| 5,301,001 A | 4/1994 | Murphy et al. | |
| 5,312,425 A | 5/1994 | Evans et al. | |
| 5,313,949 A | 5/1994 | Yock | |
| 5,313,957 A | 5/1994 | Little | |
| 5,319,492 A | 6/1994 | Dorn et al. | |
| 5,321,501 A | 6/1994 | Swanson et al. | |
| 5,325,198 A | 6/1994 | Hartley et al. | |
| 5,336,178 A | 8/1994 | Kaplan et al. | |
| 5,346,689 A | 9/1994 | Peyman et al. | |
| 5,348,017 A | 9/1994 | Thornton et al. | |
| 5,348,481 A | 9/1994 | Ortiz | |
| 5,353,798 A | 10/1994 | Sieben | |
| 5,358,409 A | 10/1994 | Obara | |
| 5,358,478 A | 10/1994 | Thompson et al. | |
| 5,368,037 A | 11/1994 | Eberle et al. | |
| 5,373,845 A | 12/1994 | Gardineer et al. | |
| 5,373,849 A | 12/1994 | Maroney et al. | |
| 5,375,602 A | 12/1994 | Lancee et al. | |
| 5,377,682 A | 1/1995 | Ueno et al. | |
| 5,383,853 A | 1/1995 | Jung et al. | |
| 5,387,193 A | 2/1995 | Miraki | |
| 5,396,328 A | 3/1995 | Jestel et al. | |
| 5,397,355 A | 3/1995 | Marin et al. | |
| 5,405,377 A | 4/1995 | Cragg | |
| 5,411,016 A | 5/1995 | Kume et al. | |
| 5,419,777 A | 5/1995 | Hofling | |
| 5,421,338 A | 6/1995 | Crowley et al. | |
| 5,423,806 A | 6/1995 | Dale et al. | |
| 5,427,118 A | 6/1995 | Nita et al. | |
| 5,431,673 A | 7/1995 | Summers et al. | |
| 5,436,759 A | 7/1995 | Dijaili et al. | |
| 5,439,139 A | 8/1995 | Brovelli | |
| 5,443,457 A | 8/1995 | Ginn et al. | |
| 5,453,575 A | 9/1995 | O'Donnell et al. | |
| 5,456,693 A | 10/1995 | Conston et al. | |
| 5,459,570 A | 10/1995 | Swanson et al. | |
| 5,480,388 A | 1/1996 | Zadini et al. | |
| 5,485,845 A | 1/1996 | Verdonk et al. | |
| 5,492,125 A | 2/1996 | Kim et al. | |
| 5,496,997 A | 3/1996 | Pope | |
| 5,507,761 A | 4/1996 | Duer | |
| 5,512,044 A | 4/1996 | Duer | |
| 5,514,128 A | 5/1996 | Hillsman et al. | |
| 5,529,674 A | 6/1996 | Hedgcoth | |
| 5,541,730 A | 7/1996 | Chaney | |
| 5,546,717 A | 8/1996 | Penczak et al. | |
| 5,546,948 A | 8/1996 | Hamm et al. | |
| 5,565,332 A | 10/1996 | Hoogenboom et al. | |
| 5,573,520 A | 11/1996 | Schwartz et al. | |
| 5,581,638 A | 12/1996 | Givens et al. | |
| 5,586,054 A | 12/1996 | Jensen et al. | |
| 5,592,939 A | 1/1997 | Martinelli | |
| 5,596,079 A | 1/1997 | Smith et al. | |
| 5,598,844 A | 2/1997 | Diaz et al. | |
| 5,609,606 A | 3/1997 | O'Boyle | |
| 5,630,806 A | 5/1997 | Inagaki et al. | |
| 5,651,366 A | 7/1997 | Liang et al. | |
| 5,660,180 A | 8/1997 | Malinowski et al. | |
| 5,667,499 A | 9/1997 | Welch et al. | |
| 5,667,521 A | 9/1997 | Keown | |
| 5,672,877 A | 9/1997 | Liebig et al. | |
| 5,674,232 A | 10/1997 | Halliburton | |
| 5,675,513 A * | 10/1997 | Hammer | 702/86 |
| 5,693,015 A | 12/1997 | Walker et al. | |
| 5,713,848 A | 2/1998 | Dubrul et al. | |
| 5,745,634 A | 4/1998 | Garrett et al. | |
| 5,771,895 A | 6/1998 | Slager | |
| 5,779,731 A | 7/1998 | Leavitt | |
| 5,780,958 A | 7/1998 | Strugach et al. | |
| 5,798,521 A | 8/1998 | Froggatt | |
| 5,800,450 A | 9/1998 | Lary et al. | |
| 5,803,083 A | 9/1998 | Buck et al. | |

(56) References Cited

U.S. PATENT DOCUMENTS

| | | | |
|---|---|---|---|
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,624,893 B1 * | 9/2003 | Schmit et al. ............... 356/511 |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |

(56) References Cited

U.S. PATENT DOCUMENTS

| | | |
|---|---|---|
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |

(56) References Cited

U.S. PATENT DOCUMENTS

| | | |
|---|---|---|
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |

(56) References Cited

U.S. PATENT DOCUMENTS

| | | |
|---|---|---|
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0085543 A1 | 5/2004 | Xie et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1* | 12/2004 | Izatt ........................... 356/450 |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1* | 2/2006 | de Boer et al. ............... 356/479 |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1* | 11/2006 | Kleen et al. .................. 600/425 |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0055591 A1* | 3/2008 | Walton ........................ 356/237.1 |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |

(56) References Cited

U.S. PATENT DOCUMENTS

| | | |
|---|---|---|
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0130950 A1* | 6/2008 | Miklos et al. ............... 382/103 |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1* | 5/2009 | Petersen et al. ............... 356/477 |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |

(56) References Cited

U.S. PATENT DOCUMENTS

| | | |
|---|---|---|
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2178442 A1 | 4/2010 |
| EP | 2438877 A2 | 4/2012 |
| GB | 2280261 A | 1/1995 |
| JP | 2000-037355 A | 2/2000 |
| JP | 2000-262461 A | 9/2000 |
| JP | 2000-292260 A | 10/2000 |
| JP | 2000-329534 A | 11/2000 |
| JP | 2001-125009 A | 5/2001 |
| JP | 2001-272331 A | 10/2001 |
| JP | 2002-503134 A | 1/2002 |
| JP | 2002-088660 A | 3/2002 |
| JP | 2002-523162 A | 7/2002 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2004004080 A | 1/2004 |
| JP | 2004-510132 A | 4/2004 |
| JP | 2004-528111 A | 9/2004 |
| JP | 2005-274380 A | 10/2005 |
| JP | 2005-533610 A | 11/2005 |
| JP | 2006-184284 A | 7/2006 |
| JP | 2006-266797 A | 10/2006 |
| JP | 2006-313158 A | 11/2006 |
| JP | 2007-510143 A | 4/2007 |
| JP | 2009-233001 A | 10/2009 |
| JP | 2009-536425 A | 10/2009 |
| JP | 2010014459 A | 1/2010 |
| JP | 2010-516302 A | 5/2010 |
| JP | 2010-516304 A | 5/2010 |
| JP | 2011-056786 A | 3/2011 |
| JP | 2011-508677 A | 3/2011 |
| JP | 2013-546256 A | 12/2013 |
| JP | 2014-501163 A | 1/2014 |
| JP | 2014-506806 A | 3/2014 |
| WO | 89/06781 A1 | 7/1989 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/44296 A1 | 8/2000 |
| WO | 01/11409 A2 | 2/2001 |
| WO | 03/032936 A1 | 4/2003 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004096049 A2 | 11/2004 |
| WO | 2005/047813 A1 | 5/2005 |
| WO | 2005/106695 A2 | 11/2005 |
| WO | 2006/016434 A1 | 2/2006 |
| WO | 2006/029634 A2 | 3/2006 |
| WO | 2006/037132 A1 | 4/2006 |
| WO | 2006/039091 A1 | 4/2006 |
| WO | 2006/061829 A1 | 6/2006 |
| WO | 2006068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/060973 A1 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |

(56) References Cited

FOREIGN PATENT DOCUMENTS

| | | |
|---|---|---|
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/006886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

DC Adler, et al., "Phase-Sensitive Optical Coherence Tomography at up to 370,000 Lines Per Second Using Buffered Fourier Domain Mode-Locked Lasers", Optics Letters, vol. 32, No. 6, pp. 626-628, (2007). Abstract Only.
Eigenwillig et al., "K-Space Linear Fourier Domain Mode Locked Laser and Applications for Optical Coherence Tomography", Optics Express, vol. 16, No. 12, pp. 8916-8937, (2008).
Herget et al., "Infrared Spectrum of Hydrogen Fluoride: Line Positions and Line Shapes. Part II. Treatment of Data and Results", Journal of the Optical Society of America, vol. 52, pp. 1113-1117, (1962).
Huber et al., "Amplified, Frequency Swept Lasers for Frequency Domain Reflectometry and OCT Imaging: Design and Scaling Principles", Optics Express, vol. 13, No. 9, pp. 3513-3528, (2005).
Huber et al., "Fourier Domain Mode Locking (FDML): A New Laser Operating Regime and Applications for Optical Coherence Tomography", Optics Express, vol. 14, No. 8, pp. 3225-3237, (2006).
MA Choma, et al., "Sensitivity Advantage of Swept Source and Fourier Domain Optical Coherence Tomography", Optics Express, vol. 11, No. 18, pp. 2183-2189, (2003).
Oldenburg et al., "Fast-Fourier-Domain Delay Line for In Vivo Optical Coherence Tomography with a Polygonal Scanner", Applied Optics, vol. 42, No. 22, pp. 4606-4611, (2003).
Sarunic et al., "Instantaneous Complex Conjugate Resolved Spectral Domain and Swept-Source OCT Using 3×3 Fiber Couplers", Optics Express, vol. 13, No. 3, pp. 957-967, (2005).
SMRM Nezam, "High Speed Polygon-Scanner-Based Wavelength-Swept Laser Source in the Telescope-Less Configurations with Application in Optical Coherence Tomography", Optics Letters, vol. 33, No. 15, pp. 1741-1743, (2008). Abstract Only.
Vakoc et al., "Phase-Resolved Optical Frequency Domain Imaging:", Optics Express, vol. 13, No. 14, pp. 5483-5493, (2005).
Written Opinion for International (PCT) Patent Application No. PCT/US2008/070010, mailed Oct. 8, 2008.
International Search Report and Written Opinion mailed on Apr. 9, 2014, for International Patent Application No. PCT/US13/75089, filed Dec. 13, 2013 (7 pages).
Larin et al., 2004, Measurement of Refractive Index Variation of Physiological Analytes using Differential Phase OCT, Proc of SPIE 5325:31-34.
International Search Report and Written Opinion mailed on Feb. 28, 2014, for International Patent Application No. PCT/US13/75653, filed Dec. 17, 2013 (7 pages).
Kruth et al., 2003, Lasers and materials in selective laser sintering, Assembly Automation, 23(4):357-371.
International Search Report and Written Opinion mailed on Mar. 11, 2014, for International Patent Application No. PCT/US13/76449, filed Dec. 19, 2013 (9 pages).
Kumagai et al., 1994, Ablation of polymer films by a femtosecond high-peak-power Ti:sapphire laser at 798 nm, Applied Physics Letters, 65(14):1850-1852.
International Search Report and Written Opinion mailed on Mar. 19, 2014, for International Patent Application No. PCT/US2013/076587, filed Dec. 19, 2013 (10 pages).
Lefevre et al., 2001, Stenting of bifurcation lesions:a rational approach, J. Interv. Cardiol., 14(6):573-585.
International Search Report and Written Opinion mailed on Mar. 7, 2014, for International Patent Application No. PCT/US2013/076512, filed Dec. 19, 2013 (8 pages).
Fischler et al., 1973, The representation and matching of pictorial structures, IEEE Transactions on Computer 22:67-92.
Canny, 1986, A computational approach to edge detection, IEEE Trans. Pattern Anal. Mach. Intell. 8:679-698.
Marks et al., 1992, By-Passing Immunization:Building High Affinity Human Antibodies by Chain Shuffling, BioTechnol., 10:779-783.
Othonos, 1997, Fiber Bragg gratings, Review of Scientific Instruments 68(12):4309-4341.
Maruno et al., 1991, Fluorine containing optical adhesives for optical communications systems, J. Appl. Polymer. Sci. 42:2141-2148.
Kheir et al., 2012, Oxygen Gas-Filled Microparticles Provide Intravenous Oxygen Delivery, Science Translational Medicine 4(140):140ra88 (10 pages).
McCafferty et al., 1990, Phage antibodies: filamentous phage displaying antibody variable domains, Nature 348:552-554.
Larin et al., 2002, Noninvasive Blood Glucose Monitoring with Optical Coherence Tomography: a pilot study in human subjects, Diabetes Care, 25(12):2263-7.
Nissen, 2001, Coronary Angiography and Intravascular Ultrasound, American Journal of Cardiology, 87(suppl):15A-20A.
Turk et al., 1991, Eigenfaces for Recognition, Journal of Cognitive Neuroscience 3(1):71-86.
Nitenberg et al., 1995, Coronary vascular reserve in humans: a critical review of methods of evaluation and of interpretation of the results, Eur Heart J. 16(Suppl 1):7-21.
Mendieta et al., 1996, Complementary sequence correlations with applications to reflectometry studies, Instrumentation and Development 3(6):37-46.
Oesterle et al., 1986, Angioplasty at coronary bifurcations: single-guide, two-wire technique, Cathet Cardiovasc Diagn., 12:57-63.
Morrison et al., 1984, Chimeric human antibody molecules: mouse antigen-binding domains with human constant region domains, PNAS 81:6851-6855.
Oldenburg et al., 2003, Fast-Fourier-Domain Delay Line for In Vivo Optical Coherence Tomography with a Polygonal Scanner, Applied Optics, 42(22):4606-4611.
Okuno et al., 2003, Recent Advances in Optical Switches Using Silica-based PLC Technology, NTT Technical Review 1(7):20-30.
Pain et al., 1981, Preparation of protein A-peroxidase mono conjugate using a heterobifunctional reagent, and its use in enzyme immunoassays, J Immunol Methods, 40:219-30.
Pasquesi et al., 2006, In vivo detection of exercise induced ultrastructural changes in genetically-altered murine skeletal muscle using polarization-sensitive optical coherence tomography, Optics Express 14(4):1547-1556.
Persson et al., 1985, Acoustic impedance matching of medical ultrasound transducers, Ultrasonics, 23(2):83-89.
Amini et al., 1990, Using dynamic programming for solving variational problems in vision, IEEE Transactions on Pattern Analysis and Machine Intelligence, 12(9):855-867.
Kersey et al., 1991, Polarization insensitive fiber optic Michelson interferometer, Electron. Lett. 27:518-520.

(56) References Cited

OTHER PUBLICATIONS

Cavalli et al., 2010, Nanosponge formulations as oxygen delivery systems, International Journal of Pharmaceutics 402:254-257.
Mindlin et al., 1936, A force at a point of a semi-infinite solid, Physics, 7:195-202.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
International Search Report and Written Opinion mailed on Apr. 23, 2014, for International Patent Application No. PCT/US2013/075328, filed Dec. 16, 2013 (8 pages).
Tanimoto et al., 2008, A novel approach for quantitative analysis of intracoronary optical coherence tomography: high inter-observer agreement with computer-assisted contour detection, Cathet Cardiovascular Intervent., 72(2):228-235.
International Search Report and Written Opinion mailed on Mar. 10, 2014, for International Patent Application No. PCT/US2013/076212, filed Dec. 18, 2013 (8 pages).
Munson et al., 1980, Ligand: a versatile computerized approach for characterization of ligand-binding systems, Analytical Biochemistry, 107:220-239.
International Search Report and Written Opinion mailed on Mar. 7, 2014, for International Patent Application No. PCT/US2013/076304, filed Dec. 18, 2013 (9 pages).
Smith et al., 1989, Absolute displacement measurements using modulation of the spectrum of white light in a Michelsor interferometer, Applied Optics, 28(16):3339-3342.
Jakobovits et al., 1993, Analysis of homozygous mutant chimeric mice:deletion of the immunoglobulin heavy-chain joining region blocks B-cell development and antibody production, PNAS USA 90:2551-255.
Milstein et al., 1983, Hybrid hybridomas and their use in immunohistochemistry, Nature 305:537-540.
Kohler et al., 1975, Continuous cultures of fused cells secreting antibody of predefined specificity, Nature, 256:495-7.
Soller, 2003, Polarization diverse optical frequency domain interferometry:All coupler implementation, Bragg Grating, Photosensitivity, and Poling in Glass Waveguides Conference MB4:30-32.
Mamas et al., 2010, Resting Pd/Pa measured with intracoronary pressure wire strongly predicts fractional flow reserve, Journal of Invasive Cardiology 22(6):260-265.
Stenqvist et al., 1983, Stiffness of central venous catheters, Acta Anaesthesiol Scand., 2:153-157.
Nygren, 1982, Conjugation of horseradish peroxidase to Fab fragments with different homobifunctional and heterobifunctional cross-linking reagents. A comparative study, J. Histochem. and Cytochem. 30:407-12.
Sutcliffe et al., 1986, Dynamics of UV laser ablation of organic polymer surfaces, Journal of Applied Physics, 60(9):3315-3322.
Placht et al., 2012, Fast time-of-flight camera based surface registration for radiotherapy patient positioning, Medical Physics 39(1):4-17.
Vakhtin et al., 2003, Common-path interferometer for frequency-domain optical coherence tomography, Applied Optics, 42(34):6953-6958.
D'Agostino et al., 2001, Validation of the Framingham coronary heart disease prediction score: results of a multiple ethnic group investigation, JAMA 286:180-187.
Verhoeyen et al., 1988, Reshaping human antibodies: grafting an antilysozyme activity, Science, 239:1534-1536.
International Search Report and Written Opinion mailed Mar. 11, 2014, for International Patent Application No. PCT/US13/75675, filed Dec. 17, 2013 (7 pages).

Wang et al., 2009, Robust Guidewire Tracking in Fluoroscopy, IEEE Conference on Computer Vision and Pattern Recognition—CVPR 2009:691-698.
International Search Report and Written Opinion mailed on Mar. 18, 2014, for International Patent Application No. PCT/US2013/076788, filed Dec. 20, 2013 (7 pages).
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Karp et al., 2009, The benefit of time-of-flight in PET imaging, J Nucl Med 49:462-470.
Felzenszwalb et al., 2005, Pictorial Structures for Object Recognition, International Journal of Computer Vision, 61(1):55-79.
Goel et al., 2006, Minimally Invasive Limited Ligation Endoluminal-assisted Revision (MILLER) for treatment of dialysis access-associated steal syndrome, Kidney Int 70(4):765-70.
Juviler et al., 2008, Anorectal sepsis and fistula-in-ano, Surgical Technology International, 17:139-149.
Bain, 2011, Privacy protection and face recognition, Chapter 3, Handbook of Face Recognition, Stan et al., Springer-Verlag.
Kirkman, 1991, Technique for flow reduction in dialysis access fistulas, Surg Gyn Obstet, 172(3):231-3.
International Search Report and Written Opinion mailed on Feb. 21, 2014, for International Patent Application No. PCT/US2013/076965, filed Dec. 20, 2013 (6 pages).
Wyawahare et al., 2009, Image registration techniques: an overview, International Journal of Signal Processing, Image Processing and Pattern Recognition, 2(3):11-28.
Little et al., 1991, The underlying coronary lesion in myocardial infarction:implications for coronary angiography, Clinica Cardiology, 14(11):868-874.
Suzuki, 2013, A novel guidewire approach for handling acute-angle bifurcations, J Inv Cardiol 25(1):48-54.
Evans et al., 2006, Optical coherence tomography to identify intramucosa carcinoma and high-grade dysplasia in Barrett's esophagus, Clin Gast Hepat 4(1):38-43.
West et al., 1991, Arterial insufficiency in hemodialysis access procedures: correction by banding technique, Transpl Proc 23(2):1838-40.
Bail et al., 1996, Optical coherence tomography with the "Spectral Radar"-Fast optical analysis in volume scatterers by short coherence interferometry, Optics Letters 21(14):1087-1089.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
International Search Report and Written Opinion mailed on Jan. 16, 2009, for International Patent Application No. PCT/US08/78963 filed on Oct. 6, 2008 (7 Pages).
International Search Report and Written Opinion mailed on Jul. 30, 2014, for International Patent Application No. PCT/US14/21659, filed Mar. 7, 2014 (15 pages).
Yasuno et al., 2004, Polarization-sensitive complex Fourier domain optical coherence tomography for Jones matrix imaging of biological samples, Applied Physics Letters 85(15):3023-3025.
Maintz et al., 1998, An Overview of Medical Image Registration Methods, Technical Report UU-CS, (22 pages).
Zhang et al., 2004, Full range polarization-sensitive Fourier domain optical coherence tomography, Optics Express, 12(24):6033-6039.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Fatemi et al., 1999, Vibro-acoustography: an imaging modality based on ultrasound-stimulated acoustic emission, PNAS U.S.A., 96(12):6603-6608.
Owens et al., 2007, A Survey of General-Purpose Computation on Graphics Hardware, Computer Graphics Forum 26(1):80-113.

(56) References Cited

OTHER PUBLICATIONS

Griffiths et al., 1993, Human anti-self antibodies with high specificity from phage display libraries, The EMBO Journal, 12:725-734.
Kelly et al., 2005, Detection of Vascular Adhesion Molecule-1 Expression Using a Novel Multimodal Nanoparticle, Circulation Research 96:327-336.
Harrison et al., 2011, Guidewire Stiffness: What's in a name?, J Endovasc Ther, 18(6):797-801.
Khuri-Yakub et al., 2011, Capacitive micromachined ultrasonic transducers for medical imaging and therapy, J Micromech Microeng. 21(5):054004-054014.
Rollins et al., 1998, In vivo video rate optical coherence tomography, Optics Express 3:219-229.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Zitova et al., 2003, Image registration methods: A survey. Image and Vision Computing, 21(11):977-1000.
Brown, 1992, A survey of image registration techniques, ACM Computing Surveys 24(4):325-376.
Wegener, 2011, 3D Photonic Metamaterials and Invisibility Cloaks: The Method of Making, MEMS 2011, Cancun, Mexico, Jan. 23-27, 2011.
Loo, 2004, Nanoshell Enabled Photonics-Based Imaging and Therapy of Cancer, Technology in Cancer Research & Treatment 3(1):33-40.
Jiang et al., 1992, Image registration of multimodality 3-D medical images by chamfer matching, Proc. SPIE 1660, Biomedical Image Processing and Three-Dimensional Microscopy, 356-66.
Bouma et al., 1999, Power-efficient nonreciprocal interferometer and linear-scanning fiber-optic catheter for optical coherence tomography, Optics Letters, 24(8):531-533.
Marks et al., 1991, By-passing Immunization Human Antibodies from V-gene Libraries Displayed on Phage, J. Mol. Biol. 222:581-597.
Blanchet et al., 1993, Laser Ablation and the Production of Polymer Films, Science, 262(5134):719-721.
Mickley, 2008, Steal Syndrome-strategies to preserve vascular access and extremity, Nephrol Dial Transplant 23:19-24.
Li et al., 2000, Optical Coherence Tomography: Advanced Technology for the Endoscopic Imaging of Barrett's Esophagus, Endoscopy, 32(12):921-930.
Miller et al., 2010, The MILLER banding procedure is an effective method for treating dialysis-associated steal syndrome, Kidney International 77:359-366.
Bruining et al., 2009, Intravascular Ultrasound Registration/Integration with Coronary Angiography, Cardiology Clinics, 27(3):531-540.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Clarke et al., 1995, Hypoxia and myocardial ischaemia during peripheral angioplasty, Clinical Radiology, 50(5):301-303.
Tuzel et al., 2006, Region Covariance: A Fast Descriptor for Detection and Classification, European Conference on Computer Vision (ECCV).
David et al., 1974, Protein iodination with solid-state lactoperoxidase, Biochemistry 13:1014-1021.
Park et al., 2005, Real-time fiber-based multi-functional spectral-domain optical coherence tomography at 1.3 um., Optics Express 13(11):3931-3944.
Elghanian et al., 1997, Selective colorimetric detection of polynucleotides based on the distance-dependent optical properties of gold nanoparticles, Science, 277(5329):1078-1080.
Pepe et al., 2004, Limitations of the odds ratio in gauging the performance of a diagnostic, prognostic, or screening marker, American Journal of Epidemiology 159(9):882-890.
Gould et al., 1974, Physiologic basis for assessing critical coronary stenosis, American Journal of Cardiology, 33:87-94.
Rabbani et al., 1999, Review: Strategies to achieve coronary arterial plaque stabilization, Cardiovascular Research 41:402-417.
Tearney et al., 1997, In vivo Endoscopic Optical Biopsy with Optical Coherence Tomography, Science, 276:2037-2039.
Agresti, 1996, Models for Matched Pairs, Chapter 8, An Introduction to Categorical Data Analysis, Wiley-Interscience a John Wiley & Sons, Inc., Publication, Hoboken, New Jersey.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Jakobovits et al., 1993, Germ-line transmission and expression of a human-derived yeast artificial chromosome, Nature 362:255-258.
Communication Mechanisms for Distributed Real-Time Applications, NI Developer Zone, http://zone.ni.eom/devzone/cda/tut/p/id/3105, accessed Jul. 23, 2007.
Johnson et al., 1993, Human antibody engineering: Current Opinion in Structural Biology, 3:564-571.
Davies et al., 1993, Risk of thrombosis in human atherosclerotic plaques: role of extracellular lipid, macrophage, and smooth muscle cell content, British Heart Journal 69:377-381.
Jones et al., 1986, Replacing the complementarity-determining regions in a human antibody with those from a mouse, Nature, 321:522-525.
Ergun et al., 2003, Capacitive Micromachined Ultrasonic Transducers:Theory and Technology, Journal of Aerospace Engineering, 16(2):76-84.
Barnea et al., 1972, A class of algorithms for fast digital image registration, IEEE Trans. Computers, 21(2):179-186.
Gotzinger et al., 2005, High speed spectral domain polarization sensitive optical coherence tomography of the human retina, Optics Express 13(25):10217-10229.
Sihan et al., 2008, A novel approach to quantitative analysis of intraluminal optical coherence tomography imaging, Comput. Cardiol:1089-1092.
Bonnema, 2008, Imaging Tissue Engineered Blood Vessel Mimics with Optical Tomography, College of Optical Sciences dissertation, University of Arizona (252 pages).
Karapatis et al., 1998, Direct rapid tooling:a review of current research, Rapid Prototyping Journal, 4(2):77-89.
International Search Report and Written Opinion mailed on Apr. 14, 2014, for International Patent Application No. PCT/US2013/076148, filed Dec. 18, 2013 (8 pages).
Kozbor et al., 1984, A human hybrid myeloma for production of human monoclonal antibodies, J. Immunol., 133:3001-3005.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Abdi et al., 2010, Principal component analysis, Wiley Interdisciplinary Reviews: Computational Statistics 2:433-459.
Robbin et al., 2002, Hemodialysis Arteriovenous Fistula Maturity: US Evaluation, Radiology 225:59-64.
Akasheh et al., 2004, Development of piezoelectric micromachined ultrasonic transducers, Sensors and Actuators A Physical, 111:275-287.
Breiman, 2001, Random forests, Machine Learning 45:5-32.
Satiani et al., 2009, Predicted Shortage of Vascular Surgeons in the United States, J. Vascular Surgery 50:946-952.
Fookes et al., 2002, Rigid and non-rigid image registration and its association with mutual information:A review, Technical Report ISBN:1 86435 569 7, RCCVA, QUT.
Schneider et al., 2006, T-banding: A technique for flow reduction of a hyper-functioning arteriovenous fistula, J Vasc Surg. 43(2):402-405.

(56) References Cited

OTHER PUBLICATIONS

Collins, 1993, Coronary flow reserve, British Heart Journal 69:279-281.
Sen et al., 2012, Development and validation of a new adenosine-independent index of stenosis severity from coronary wave-intensity analysis, Journal of the American College of Cardiology 59(15):1392-1402.
Cook, 2007, Use and misuse of receiver operating characteristic curve in risk prediction, Circulation 115(7):928-35.
Setta et al., 2005, Soft versus firm embryo transfer catheters for assisted reproduction: a systematic review and meta-analysis, Human Reproduction, 20(11):3114-3121.
Davies et al., 1985, Plaque fissuring—the cause of acute myocardial infarction, sudden ischaemic death, and crescendo angina, British Heart Journal 53:363-373.
Seward et al., 1996, Ultrasound Cardioscopy: Embarking on New Journey, Mayo Clinic Proceedings 71(7):629-635.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Shen et al., 2006, Eigengene-based linear discriminant model for tumor classification using gene expression microarray data, Bioinformatics 22(21):2635-2642.
Siwy et al., 2003, Electro-responsive asymmetric nanopores in polyimide with stable ion-current signal, Applied Physics A: Materials Science & Processing 76:781-785.
Fleming et al., 2010, Real-time monitoring of cardiac radio-frequency ablation lesion formation using an optical coherence tomography forward-imaging catheter, Journal of Biomedical Optics 15(3):030516-1 (3 pages).
Smith, 1997, The Scientist and Engineer's Guide to Digital Signal Processing, California Technical Publishing, San Diego, CA:432-436.
Grund et al., 2010, Analysis of biomarker data:logs, odds, ratios and ROC curves, Curr Opin HIV AIDS 5(6):473-479.
Griffiths et al., 1994, Isolation of high affinity human antibodies directly from large synthetic repertoires, The EMBO Journal, 13(14):3245-3260.
Song et al., 2012, Active tremor cancellation by a "Smart" handheld vitreoretinal microsurgical tool using swept source optical coherence tomography, Optics Express, 20(21):23414-23421.
Strobl et al., 2009, An Introduction to Recursive Partitioning:Rationale, Application and Characteristics of Classification and Regression Trees, Bagging and Random Forests, Psychol Methods., 14(4):323-348.
International Search Report and Written Opinion mailed Nov. 2, 2012, for International Patent Application No. PCT/US12/53168, filed Aug. 30, 2013 (8 pages).
Strickland, 1970, Time-Domain Reflectometer Measurements, Tektronix, Beaverton, OR, (107 pages).
International Search Report and Written Opinion mailed Mar. 19, 2014, for International Patent Application No. PCT/US13/075353, filed Dec. 16, 2013 (8 pages).
Tonino et al., 2009, Fractional flow reserve versus angiography for guiding percutaneous coronary intervention, The New England Journal of Medicine, 360:213-224.
International Search Report and Written Opinion mailed on Apr. 21, 2014, for International Patent Application No. PCT/US2013/076015, filed Dec. 18, 2013 (7 pages).
Toregeani et al., 2008, Evaluation of hemodialysis arteriovenous fistula maturation by color-flow Doppler ultrasound, J Vasc. Bras. 7(3):203-213.
International Search Report and Written Opinion mailed on Apr. 29, 2014, for International Patent Application No. PCT/US13/76093, filed Dec. 18, 2013 (6 pages).
Traunecker et al., 1991, Bispecific single chain molecules (Janusins) target cytotoxic lymphocytes on HIV infected cells EMBO J., 10:3655-3659.
International Search Report and Written Opinion mailed on Feb. 21, 2014, for International Patent Application No. PCT/US13/76053, filed Dec. 18, 2013 (9 pages).
Trolier-McKinstry et. al., 2004, Thin Film Piezoelectric for MEMS, Journal of Electroceramics 12:7-17.
International Search Report and Written Opinion mailed on Feb. 27, 2014, for International Patent Application No. PCT/US13/75416, filed Dec. 16, 2013 (7 pages).
Tuniz et al., 2010, Weaving the invisible thread: design of an optically invisible metamaterial fibre, Optics Express 18(17):18095-18105.
International Search Report and Written Opinion mailed on Feb. 28, 2014, for International Patent Application No. PCT/US13/75990, filed Dec. 18, 2013 (7 pages).
Urban et al., 2010, Design of a Pressure Sensor Based on Optical Bragg Grating Lateral Deformation, Sensors (Basel), 10(12):11212-11225.
International Search Report and Written Opinion mailed on Mar. 11, 2014, for International Patent Application No. PCT/US13/76173, filed Dec. 16, 2013 (9 pages).
International Search Report and Written Opinion mailed on Mar. 18, 2014, for International Patent Application No.PCT/US2013/076502, filed Dec. 19, 2013 (7 pages).
Wang et al., 2006, Multiple biomarkers for the prediction of first major cardiovascular events and death, The New England Journal of Medicine, 355(25):2631-2639.
International Search Report and Written Opinion mailed on Mar. 19, 2014, for International Patent Application No. PCT/US13/75349, filed Dec. 16, 2013 (10 pages).
Villard et al., 2002, Use of a blood substitute to determine instantaneous murine right ventricular thickening with optical coherence tomography, Circulation, 105:1843-1849.
International Search Report and Written Opinion mailed on Mar. 19, 2014, for International Patent Application No. PCT/US2013/076909, filed Dec. 20, 2013 (7 pages).
Forstner & Moonen, 1999, A metric for covariance matrices, In Technical Report of the Dpt of Geodesy and Geoinformatics, Stuttgart University, 113-128.
International Search Report and Written Opinion mailed on Mar. 7, 2014, for International Patent Application No. PCT/US2013/076480, filed Dec. 19, 2013 (8 pages).
Waterhouse et. al., 1993, Combinatorial infection and in vivo recombination: a strategy for making large phage antibody repertoires, Nucleic Acids Res., 21:2265-2266.
International Search Report and Written Opinion mailed on Mar. 7, 2014, for International Patent Application No. PCT/US2013/076531, filed Dec. 19, 2013 (10 pages).
Yaqoob et al., 2006, Methods and application areas of endoscopic optical coherence tomography, J. Biomed. Opt., 11, 063001-1-063001-19.
Wang et al., 2011, In vivo intracardiac optical coherence tomography imaging through percutaneous access: toward image-guided radio-frequency ablation, J. Biomed. Opt. 0001 16(11):110505-1 (3 pages).
Laufer, 1996, Introduction to Optics and Lasers in Engineering, Cambridge University Press, Cambridge UK:156-162.
Extended European Search Report for PCT/US2013/026834 dated Oct. 5, 2015 (6 pages).
Extended European Search Report for PCT/US2008/070010 dated Apr. 7, 2016 (13 pages).

* cited by examiner

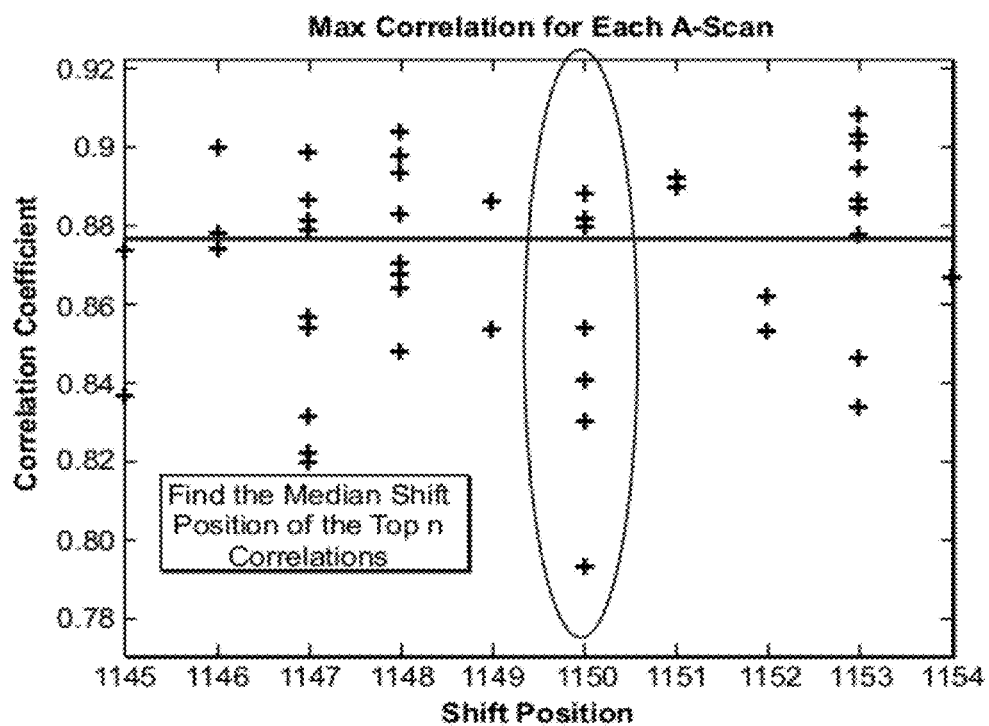
FIG. 20
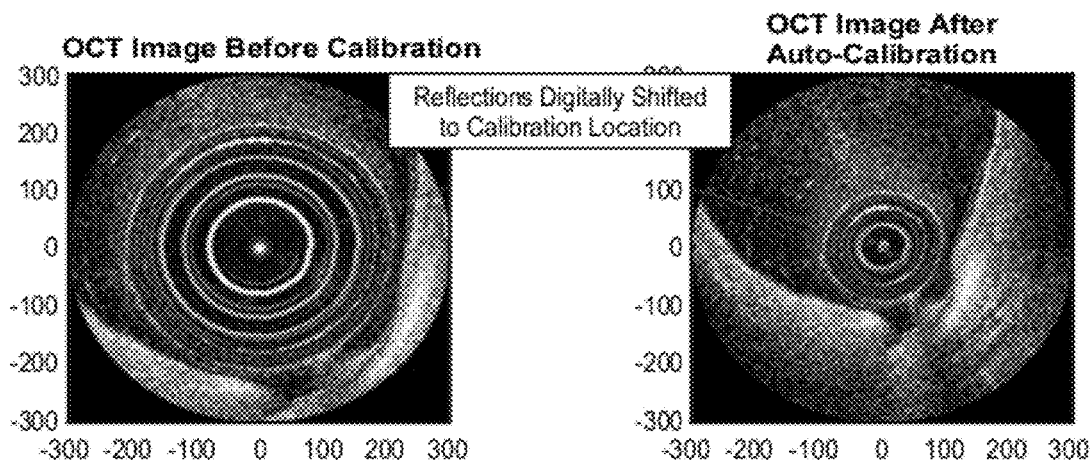
FIG. 21A
FIG. 21B

AUTOMATIC CALIBRATION SYSTEMS AND METHODS OF USE

CROSS-REFERENCE TO RELATED APPLICATIONS

This is a continuation-in-part of U.S. patent application Ser. No. 13/243,399, which was filed Sept. 23, 2011, which is a continuation of 12/172,980 (now Pat. NO. 8,049,900), which was filed Jul. 14, 2008 and which claims priority to U.S. Patent Application Ser. No. 60/949,467 filed Jul. 12, 2007, and the entirety of each of which is incorporated herein by reference.

FIELD OF THE INVENTION

The invention generally relates to calibration systems and methods of use, and more particularly to calibration systems for optical imaging systems.

BACKGROUND

Accurate Optical Coherence Tomography (OCT) measurements or dimensional analysis require the displayed tomographic image to correctly represent physical space (i.e. conversion from image pixels to physical mm). This requirement is complicated by factors such as varying object refractive indexes (catheter optics, sheath, lumen, tissue) and the arbitrary location (in z) of relevant image features due to mismatch in the interferometer's sample and reference paths.

Most current methods require the user to manually calibrate the image by adjusting the Z-Offset position (reference arm path length) until the outer diameter of the catheter sheath aligns with fixed tick marks on the screen. This method can be time consuming and lends itself to operator error. Additionally, once the catheter is shifted from the original calibrated position, the calibration can be thrown off due to time-varying mechanical strain (e.g. pullback motion or manipulation of PIM cable) or thermal changes (room temp vs. body temp).

SUMMARY OF THE INVENTION

The invention addresses the above-identified problems and relates to automatic calibration. A catheter can be calibrated, according to the invention, by taking an image in a catheter and utilizing a template to identify the position of the catheter reflection lines. Another way to calibrate a catheter is to image a catheter pullback, align the image data to ensure any shifts to the reflection positions during image acquisition are corrected, and track the reflection positions through each image frame. Yet another way to calibrate a catheter is take an image of a catheter, track the reflection lines of the catheter, not detect the reflection lines in an image, and reacquire the lost track image with a graph search step or a template matching step.

The foregoing and other features, advantages, and objects of the invention will become more apparent with reference to the disclosure that follows. The following description of exemplary embodiments, read in conjunction with the accompanying figures, is merely illustrative rather than limiting.

BRIEF DESCRIPTION OF THE DRAWINGS

The following brief descriptions are provided for a more complete understanding of the figures, but it should be understood that embodiments according to the invention are not necessarily limited to the precise arrangements and configurations shown.

FIG. 20 is a graph of the third step in the live tracking mode for finding the maximum correlation per A-scan and taking the median of the top "n" A-scans.

FIGS. 21A-21B are OCT images before and after calibrations in the fourth step by applying the digital shift to the image and scan-convert.

DETAILED DESCRIPTION OF THE INVENTION

Figure 1:
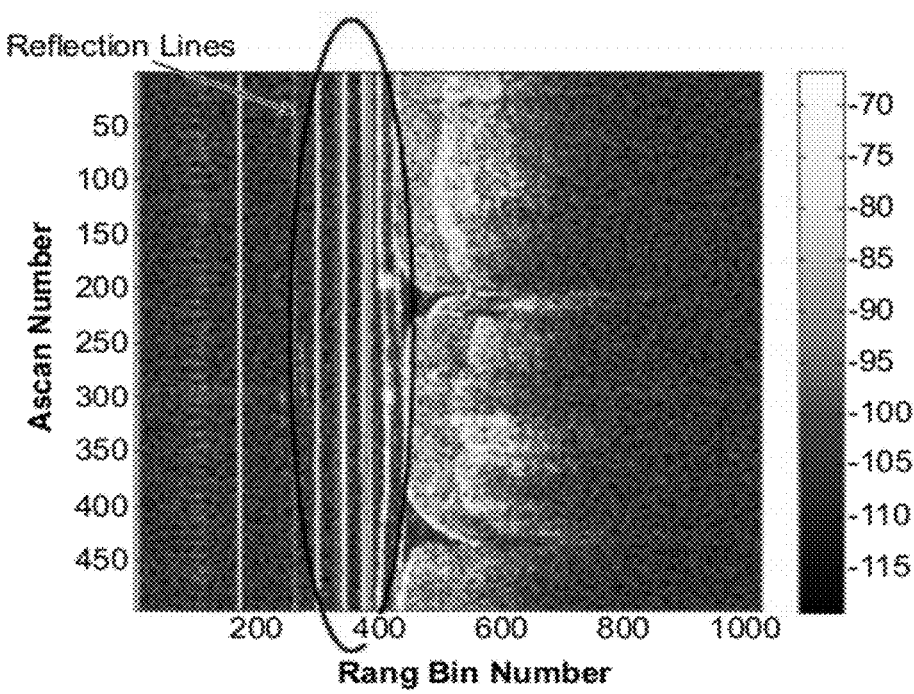
FIG. 1 is a graph showing the sample frame demonstrating catheter reflections used for calibration, in accordance with one embodiment.

In general, automatic calibration systems and methods according to the invention provide a repeatable way of detecting the internal catheter reflections and shifting the internal catheter reflections to calibrate an image. In one embodiment, the internal catheter reflections comprise reflections due to the end of the fiber optic cable, minor, lens, sheath, fluids, biological vessels, or any other objects that cause reflections and the like. The internal catheter reflections can be shifted mechanically and/or digitally. Generally, the automatic calibration comprises a first mode, a second mode, and a third mode. The calibration systems and methods update and maintain the calibration on a continuous frame-by-frame basis after an initial calibration.

An Optical Coherence Tomography (OCT) system may include a Fourier domain OCT ("FD-OCT"), sometimes known as Spectral Domain OCT ("SD-OCT"), or a Time-Domain OCT scanning ("TD-OCT"), where the optical path length of light in the reference arm of the interferometer is rapidly scanned over a distance corresponding to the imaging depth range. The OCT systems may be polarization-sensitive or phase-sensitive and adjusted accordingly. Alternatively, the imaging system may be any other optical imaging based system including, but not limited to spectroscopy, (including fluorescence, absorption, scattering, and Raman spectroscopies)

OCT Depth Calibration and Automated Range Adjustment

Circular and cylindrical OCT scanning devices, i.e. the rotation catheter scanning devices, sample physical space in an inherently polar coordinate system (e.g. radius and angle rather than length and width). Circular and cylindrical OCT scanning devices are applied to image physiological structures with cylindrical-like cross sections e.g., airways and blood vessel lumens). Digital representations of the images (i.e. arrays of pixels representing numeric values) are inherently rectangular. A method for detecting and using OCT image features, either intentionally or artifactually generated comprises automatically adjusting the depth range in polar ("radar-like") OCT images.

Polar OCT images are converted from their rectangular representation before displaying to the viewer on a video monitor or other physical display device. Additionally, if quantitative values (e.g. lumen diameters, lumen areas, circumferences, etc.) are to be measured on the polar image, then the transformation from rectangular-to-polar preserves relative distances between pixels in all dimensions (radial and angular). Generally, the OCT depth scan (y axis in rectangular coordinates) maps directly to radius and the OCT circumferential scan (x axis in rectangular coordinates) maps to some increment of 2*Pi radians (or 360°) polar angle.

For example: y=0 (the top row of the rectangular image) maps to radius=0 (the center of the polar image) and $y=y_{max}$ (the bottom row of the rectangular image) maps to radius=$y_{max}$ (the perimeter of the polar image). Likewise, x=0 (the left column in the rectangular image) maps to angle=0° and x=$x_{max}$/2 maps to approximately 180° and x=$x_{max}$ maps to an angle of approximately 359°.

For accurate quantitative dimensional measurement in polar images, pixels mapping to radius=0 represent the actual physical space at the center of the axis of rotation of the imaging probe, otherwise the polar image will be artificially warped (expanded or contracted) in the radial direction. However, in an arbitrary OCT image, the pixels at y=0 do not necessarily satisfy this requirement and must be shifted in the y-dimension until this is satisfied before mapping to a polar representation. Differential displacements (either controlled or uncontrolled) in the path length of the sample vs. reference arms of the interferometer will shift the pixels in the y-dimension.

Uncontrollable displacements can occur when using cylindrical or helical-scanning fiber-optic OCT catheters. For example, when the catheter is pushed or pulled longitudinally, the fiber-optic cable can be compressed or stretched and thus a path length displacement is incurred.

The method generally comprises automatically recognizing the uncontrolled displacement effect by searching for image features that are stationary but are not due to uncontrollable displacement, and calibrating successive OCT image data so that polar representations can be used for accurate dimensional measurements. In one embodiment, the method further comprises removing of image features in the image prior to display on a video monitor or other display device.

Image features used by the method are generated within the catheter itself (not within the imaged subject or surroundings) and appear somewhat stable in depth and consistent in intensity throughout the 360° rotation of the catheter. These image features include, but are not limited to, back reflections at interfaces between optical components (aka "ghost-lines" or "echo artifacts", these occur along the optical axis of rotating parts and thus appear as uniform circles in the polar image when no differential path length displacement occurs over the course of one catheter rotation), or reflections from the boundaries of or from within the stationary (non-rotating) catheter sheath (if it is circular in cross-sectional profile and also mechanically concentric with the rotating portion).

The embodiments disclosed herein include 3 methods for automatic calibration that utilize a plurality of back reflections to identify the required shift to achieve proper calibration. While there may be overlap between each of the 3 methods, each of the 3 methods are documented in a separate section for descriptive purposes only, and each of the 3 methods may be combined in alternative configuration, methods, parameters and the like. The first method includes an Automatic Calibration of the Z-offset, which is averaging and a general auto-calibration implementation. The second method includes an Automatic Calibration of Z-offset, which includes a Template Matching and a Graph Search method. The third method is an Automatic Calibration of Z-offset, which includes a Full Template Correlation.

Method 1: Automatic Calibration of Z-offset and Averaging. In one embodiment, steps in the automatic recognition and calibration method include: (1) Averaging the OCT image frame along the x- (i.e. angular) dimension to selectively enhance the feature(s) that are rotationally stable in the y-dimension (i.e. radius) vs. other image features generated by subject or surroundings. Efficacy of the averaging step is improved by selecting image feature(s) that have a high intensity relative to the surrounding pixels and if the subject/environment features (noise) do not have strong circumferential symmetry. In one embodiment, the method further comprises: (2) Finding image feature(s) using peak searching, correlation, thresholding, or other pattern recognition algorithms. Efficacy of the finding image features step is improved if the range over which uncontrolled path length displacements can occur is known a priori, thus limiting the required search space. In one embodiment, the method further comprises: (3) Comparing the y-value(s) of the image feature(s) found in step 2 to a pre-calibrated y-value that represents the actual physical location(s) of that image feature(s) relative to the rotational axis, or to the location of a known "conjugate image" or "aliased image" of that feature(s) when using spectral-domain OCT. In one embodiment, the method further comprises: (4) Calibrating by shifting the OCT image pixels in the y-dimension by the difference between searched image feature(s) and pre-calibrated image feature(s). Multiple features can be used to improve efficacy of the algorithm. After shifting the rectangular image in the y-dimension, mapping to polar image coordinates may take place. Radii measured to the center of the calibrated polar image represent actual radii measured to the rotational axis in physical space. Some image features due to the catheter are unwanted for effective and distraction-free display of the subject/environment features on a video monitor or other physical display device. For example, the catheter image features could overlap the subject/environment features.

In one embodiment, steps to remove (or make less noticeable) the image features include: cropping out the image feature(s) extent in the radial y-direction and in all columns/angles; calculating the average value of the pixels immediately inside and outside (above and below) of the cropped region for all columns/angles; and inserting this averaged row/circumference in the cropped location. The cropping operation can also remove subject/environment features and distorts the image in the radial dimension. This distortion makes measurement of accurate quantitative values on such images more complicated, because the measurement tool must then consider where pixels have and have not been cropped (or make the measurement on the un-cropped image).

In the calibration embodiment described above, the calibration method averages over a frame to identify a reflection, then adjusts the image digitally based on the feature location, and applies a constant shift for all A-scans within an image. An alternative method for an automatic calibration of the Z-offset uses internal catheter features that appear in the image to identify the required shift, which does not average the image intensities across a frame to find the image features, but uses a pattern of the reflections in the form of a template to identify the position of the reflections in an initial locking algorithm. "Template" generally refers to the catheter reflections pattern. This method applies a line-by-line shift to ensure that every A-scan is properly aligned for measurements in the playback mode algorithm. This method of Binary Template Matching and Graph Searching for Automatic Calibration of Z-offset is described in more detail below.

Method 2: Automatic Calibration of Z-offset and Template Matching and Graph Search.

In one embodiment, the Automatic Calibration of Z-offset comprises a first mode of calibrating catheter reflections including an initial lock step. The initial lock comprises utilizing a template to identify the position of the catheter reflection lines unique to a particular catheter, as shown in FIG. 1. The template for each catheter is stored with the specific catheter. In one embodiment, the template is stored on a Radio Frequency Identification (RFID) chip, alternatively, the template may be stored on a computer chip, and the like. Alternatively, RFID or computer chip may be removable and then be used as a portable template or medical record. Alternatively, if the catheter is approved for reuse, the Patient Interface Module or PIM may down load specific information regarding the template for the particular catheter. This template information may be stored and tracked on the catheter monitor and limit the number of uses or hours of use to a predetermined amount also stored on the catheter. In one embodiment the RFID chip may be a Maxwell ME1 or ME2 RFID chip, mounted on the connector on the proximal end of the catheter for storing information and communicating with the interface device. In an alternative embodiment, the catheter may have a second RFID chip (not shown) mounted 180 degrees from the first RFID chip of the connector so catheter can be connected to interface device at more than one circumferential orientation. The RFID chip may have a memory of 128 bytes, alternatively 1K byte, alternatively 2K bytes alternatively 4K bytes to store catheter specific information, including for example catheter serial number, name, make or model, calibration coefficients, imaging element sensitivity, time gain control, post amp gain, number of permissible uses, geographic location of permissible use, boot mode, pulse width, or expiration date of the catheter.

Figure 2A:
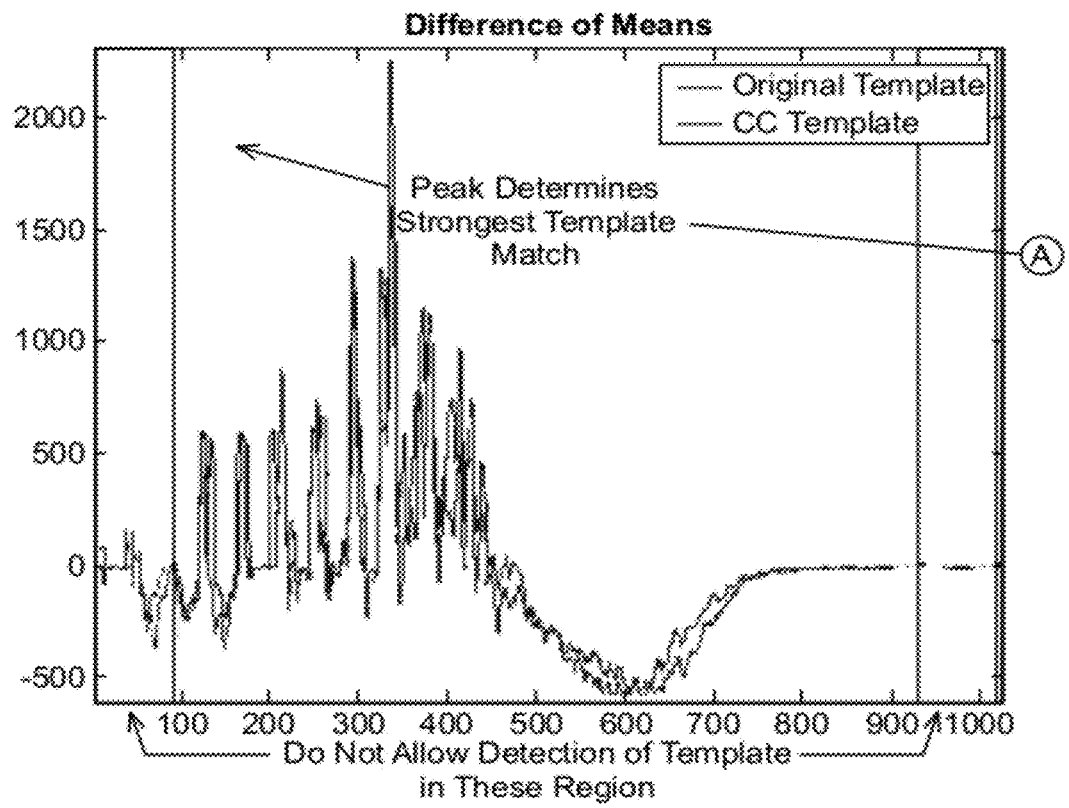
FIG. 2A is a graph of a template matching algorithm identifying a peak at bin 340, in accordance with one embodiment.
Figure 2B:
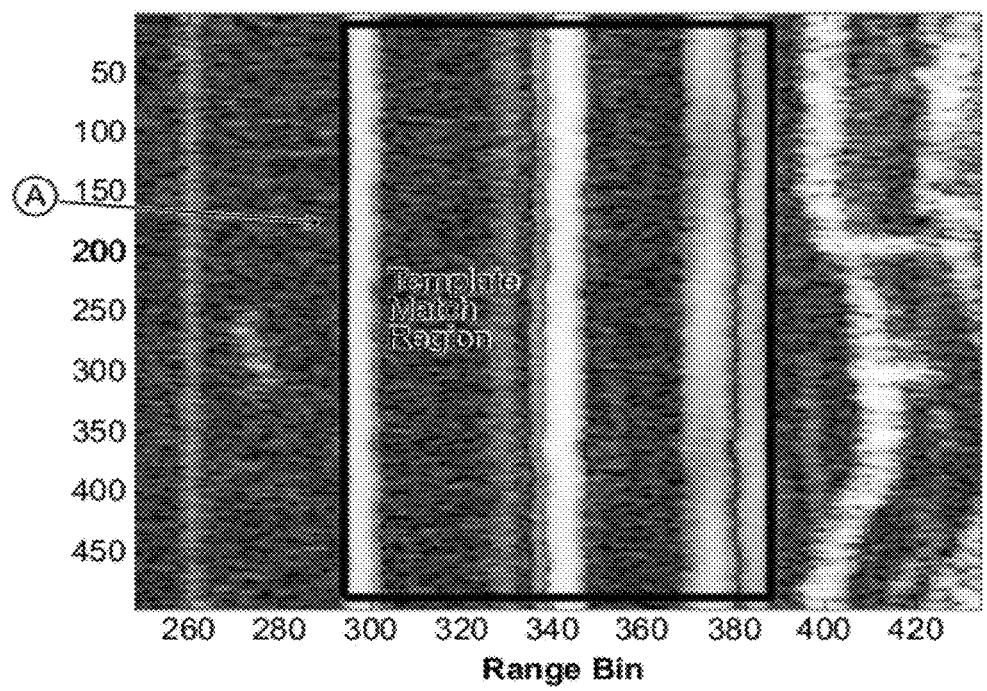
FIG. 2B is a graph of the zoomed in region A showing template match at bin 340, in accordance with one embodiment.

The template is convolved with a binary version of the gradient image and a peak is identified in a template matching step, as shown in FIG. 2A. The template matching step includes selecting a peak that corresponds to a strongest template match. In one embodiment, the peak is above a certain value to ensure that the strongest template match is identified. If no template match is identified, the Z-Offset position is adjusted and an image at the new position is evaluated with the template matching step or algorithm. Once the position of the catheter reflection lines are identified, the catheter reflection lines are shifted by adjusting the Z-Offset to move the reflections to their desired location and the image/catheter is now calibrated, as shown in FIG. 2B. In one embodiment, the adjusting Z-Offset comprises the mechanical shifting of the Variable Delay Line (VDL)). If the template matching algorithm is unable to identify a strong template match, the user is warned and given the option to retry auto-calibration or manually calibrate.

Figure 3:
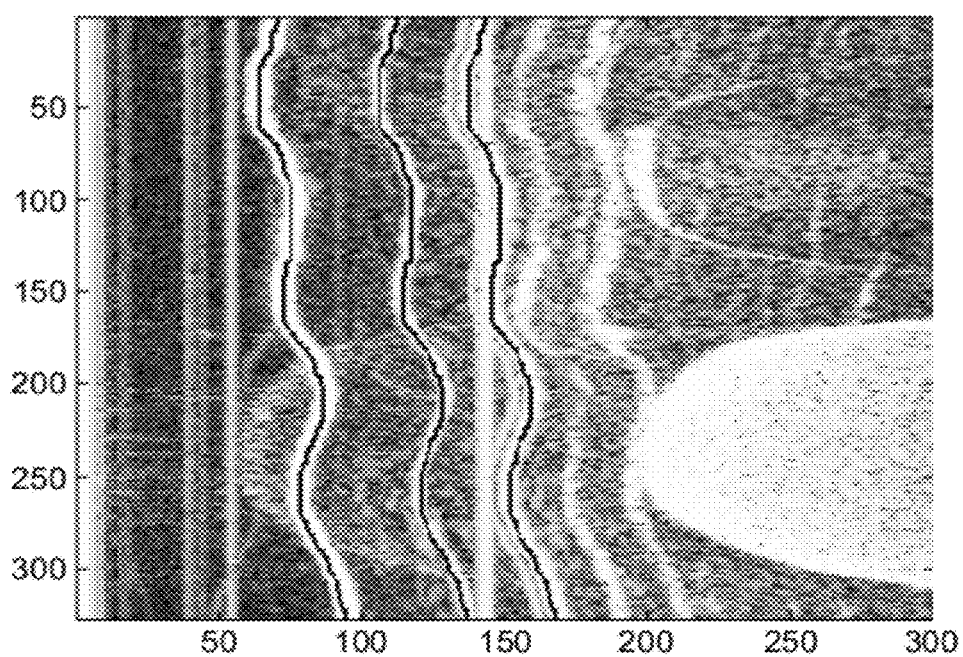
FIG. 3 is an enlarged image of reflection motion through one frame (motion due to tortuous pull back), in accordance with one embodiment.
Figure 4:
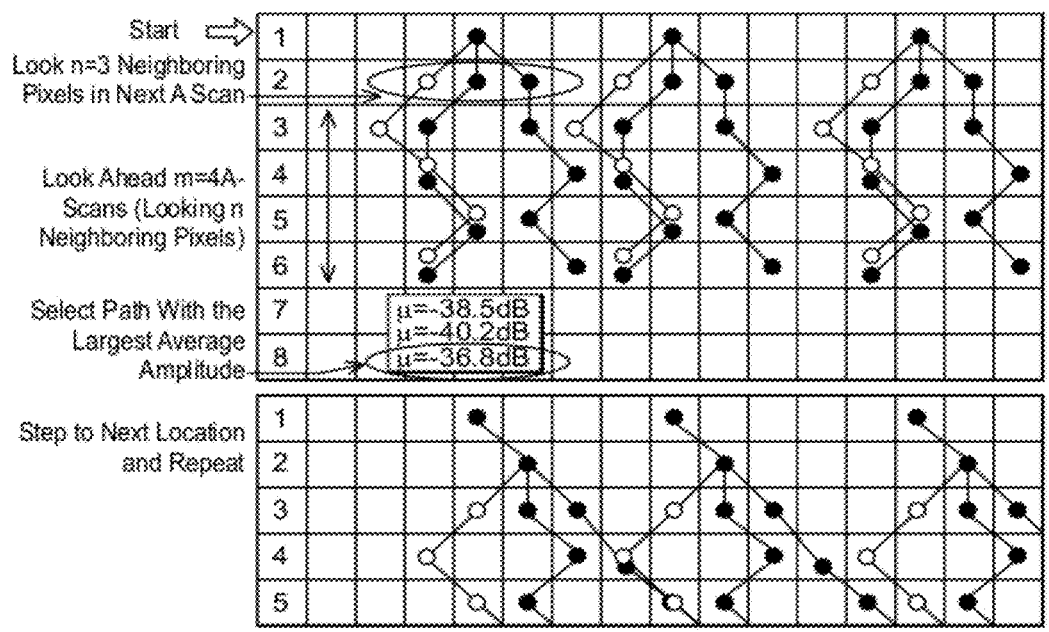
FIG. 4 is a graph search algorithm, in accordance with one embodiment.

In one embodiment of Method 2 for the Automatic Calibration of Z-offset for the Template Matching and Graph Search, the second mode of calibrating catheter reflections comprises playback tracking. Playback tracking generally includes aligning the image data after recording a catheter pullback to ensure any shifts to the reflection positions during acquisition are corrected to allow for proper analysis and/or measurements. Tracking the reflections through the recorded dataset is slightly more difficult due to the motion during pullbacks and the position of the reflections can vary significantly over a single frame. FIG. 3 demonstrates an example of significant shifting of the catheter reflections during a tortuous pullback. A graph searching step or algorithm is utilized to track the reflection through each frame. The graph search initial is identified by the template matching step or algorithm described above. Once an initial lock is acquired, the reflection lines are tracked through the image based on their amplitude and relative position. In one embodiment, the lines are tracked through the image based on their amplitude and relative position by maintaining a constant distance. The graph search step begins at the first A-scan and then looks at the neighboring pixels in the following A-scan to determine the direction for the next step. This process is then repeated for each A-scan. The algorithm also allows for "look ahead" which includes evaluating the next A-scan and looking ahead at the next "n" A-scans before determining the step direction. The black lines tracing the reflection in FIG. 3 demonstrate the results of the graph search algorithm. FIG. 4 provides a slightly more detailed explanation of the graph search algorithm. Once the lines have been traced through an entire frame they are digitally aligned and the frame is then properly calibrated for display and measurements.

Figure 5:
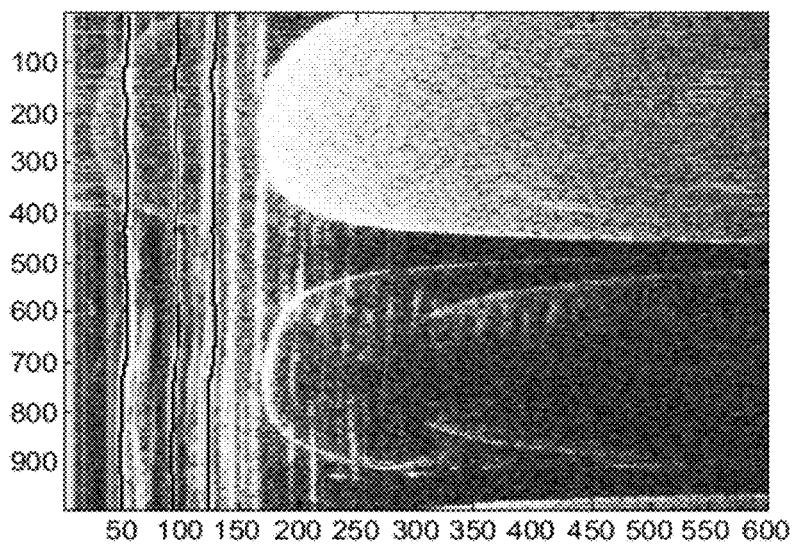
FIG. 5 is an image frame of a catheter pullback sequence and the track maintained through image frame, in accordance with one embodiment.
Figure 6:
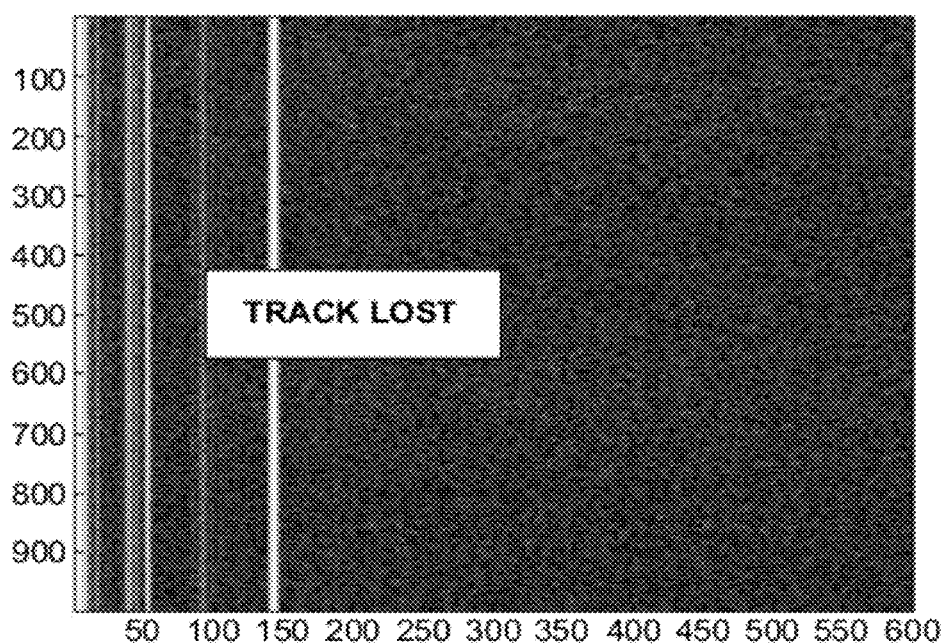
FIG. 6 is an image frame 40 of a catheter pullback sequence and the catheter reflection lines not being present and the track is lost, in accordance with one embodiment.
Figure 7:
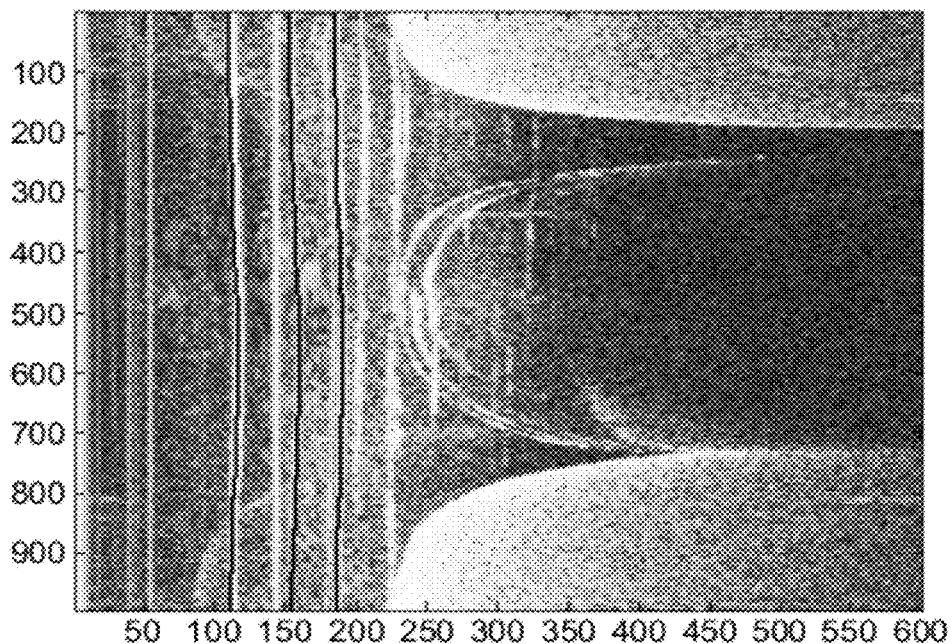
FIG. 7 is an image frame 50 of a catheter pullback sequence and the catheter reflections reappearing and the track reacquired for autocalibration, in accordance with one embodiment.

In one embodiment, the third mode of calibrating catheter reflections comprises a reacquiring lost track step. The reacquiring lost track step comprises reacquiring a track if the reflection lines are not detected in the previous image frames. As shown in FIGS. 5-7, the track of the reflections are lost during a tortuous pullback and then reacquired once the reflections reappear. To reacquire a lost track both the graph search step 220 and the template matching algorithms may be used. The graph search step expands the region of allowable solutions to search a wider number of bins for the reappearing reflections. A "guard band" is identified to limit the possible search region and prevents from locking on to the bright returns from the vessel wall. The template matching step may also be performed as described in the Initial Locking step. Once the track is reacquired, the algorithm transitions back to Playback Tracking mode to continue tracking the reflections through each subsequent frame.

Figure 8A:
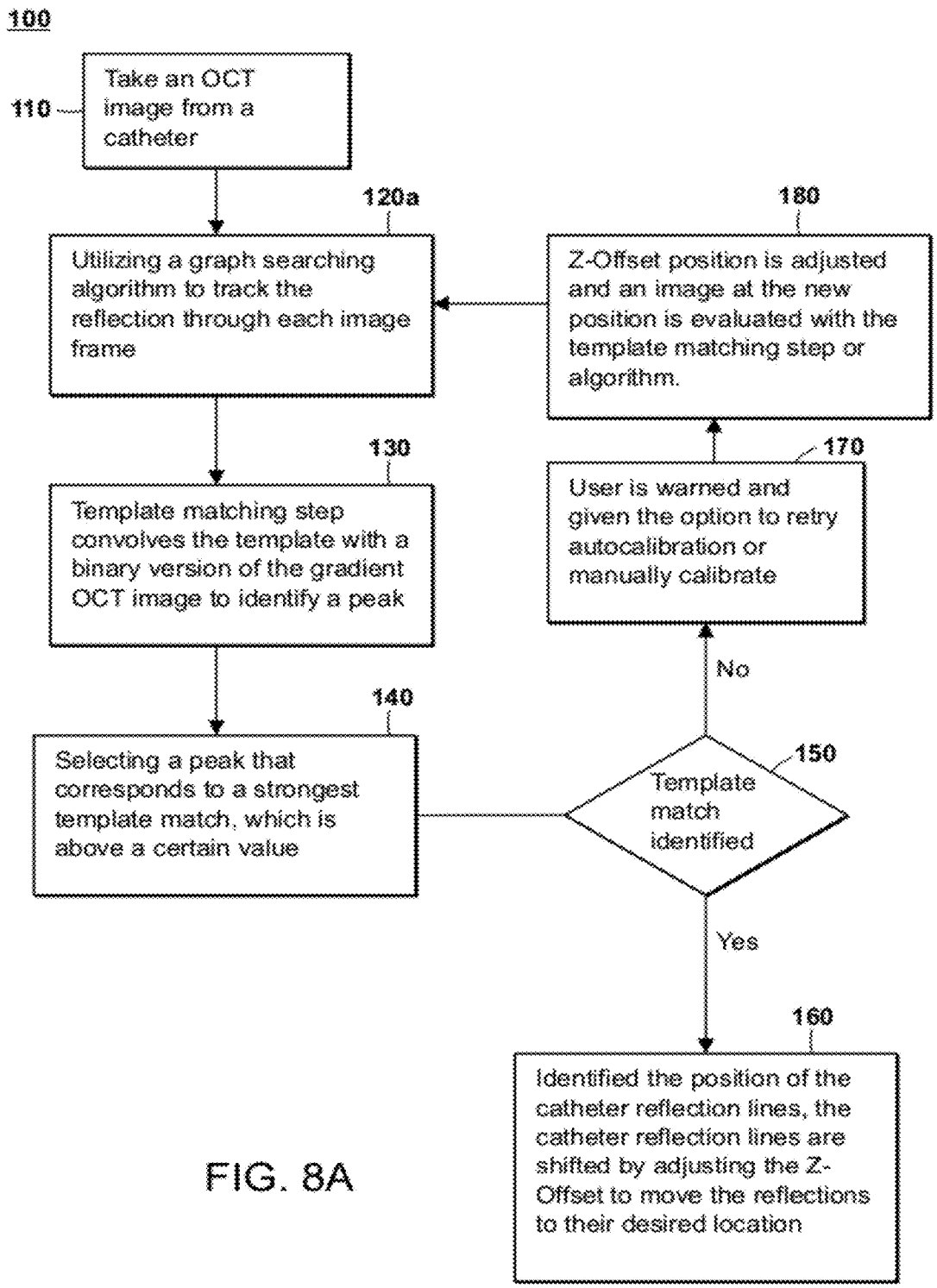
FIG. 8A is a flowchart displaying the first mode of the template matching step 100, in accordance with one embodiment.

With reference to FIG. 8A, an illustrated method of the first mode and the initial lock step 100 is shown. The process begins at step 110 by taking an OCT image in a catheter. Then, step 120 utilizes a template to identify the position of the catheter reflection lines unique to a particular catheter from a module or other software device, as shown in FIG. 2B. The template for each catheter is stored or operably accessible with the specific catheter. In one embodiment, the template is stored on a Radio Frequency Identification (RFID) chip or transponder or tag; alternatively, the template may be stored on a computer chip, cache, flash drive, and any other storage medium. The template matching step or algorithm 130 convolves the template with a binary version of the gradient OCT image and a peak is identified, as shown in FIG. 2A. The template matching step includes step 140 for selecting a peak that corresponds to a strongest template match. In one embodiment, the peak is above a certain value to ensure that the strongest template match is identified. If no template match is identified in decision 150, the method proceeds to step 170 where the Z-Offset position is adjusted and an image at the new position is evaluated with the template matching step or algorithm 130. If the template matching algorithm is unable to identify a strong match, the user is warned and given the option to retry auto-calibration or manually calibrate. If a template match is identified in decision 150, the position of the catheter reflection lines are identified, the catheter reflection lines are shifted by adjusting the Z-Offset to move the reflections to their desired location, and the image/catheter is now calibrated, as shown in FIG. 2B. In one embodiment, the adjusting Z-Offset comprises the mechanical shifting of the Variable Delay Line (VDL).

Figure 8B:
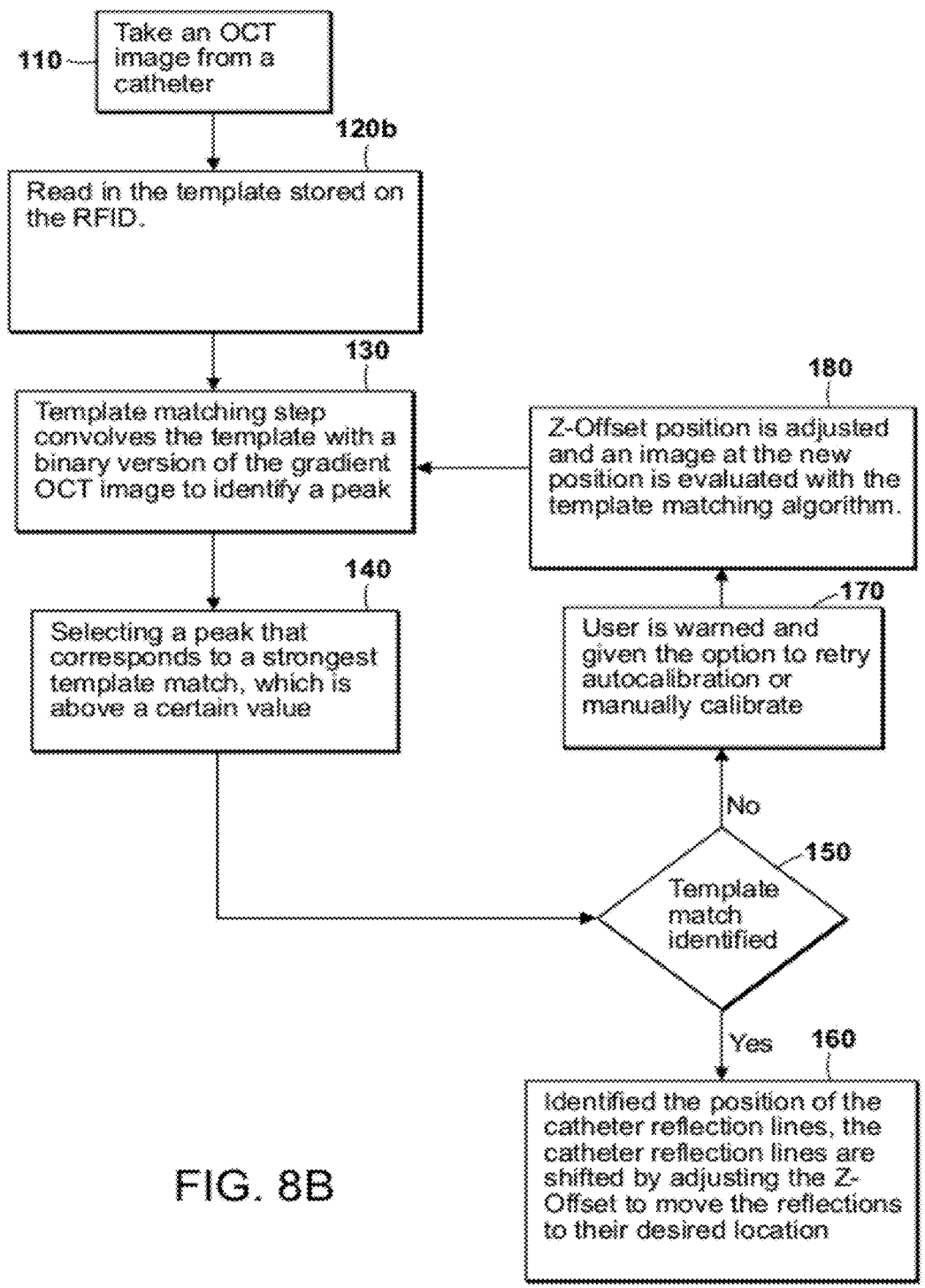
FIG. 8B is a flowchart displaying the first mode of the template matching step 100, in accordance with an alternative embodiment.

With reference to FIG. 8B, an alternative method of the first mode and the initial lock step 100b is shown. The process 100b begins similar as process 100a at step 110 by taking an OCT image in a catheter. Then, step 120 utilizes a template to identify the position of the catheter reflection lines unique to a particular catheter from a module or other software device, as shown in FIG. 2B. The template for each catheter is stored or operably accessible with the specific catheter. In one embodiment, the template is stored on a Radio Frequency Identification (RFID) chip or transponder or tag; alternatively, the template may be stored on a computer chip, cache, flash drive, and any other storage medium. The template matching step 130 convolves the template with a binary version of the gradient OCT image and a peak is identified, as shown in FIG. 2A. The template matching step includes step 140 for selecting a peak that corresponds to a strongest template match. In one embodiment, the peak is above a certain value to ensure that the strongest template match is identified. If no template match is identified in decision 150, the method proceeds to step 170 where the Z-Offset position is adjusted and an image at the new position is evaluated with the template matching step 130. If the template matching algorithm is unable to identify a strong template match, the user is warned and given the option to retry auto-calibration or manually calibrate. If a template match is identified in decision 150, the position of the catheter reflection lines are identified, the catheter reflection lines are shifted by adjusting the Z-Offset to move the reflections to their desired location, and the image/catheter is now calibrated, as shown in FIG. 2B.

Figure 9:
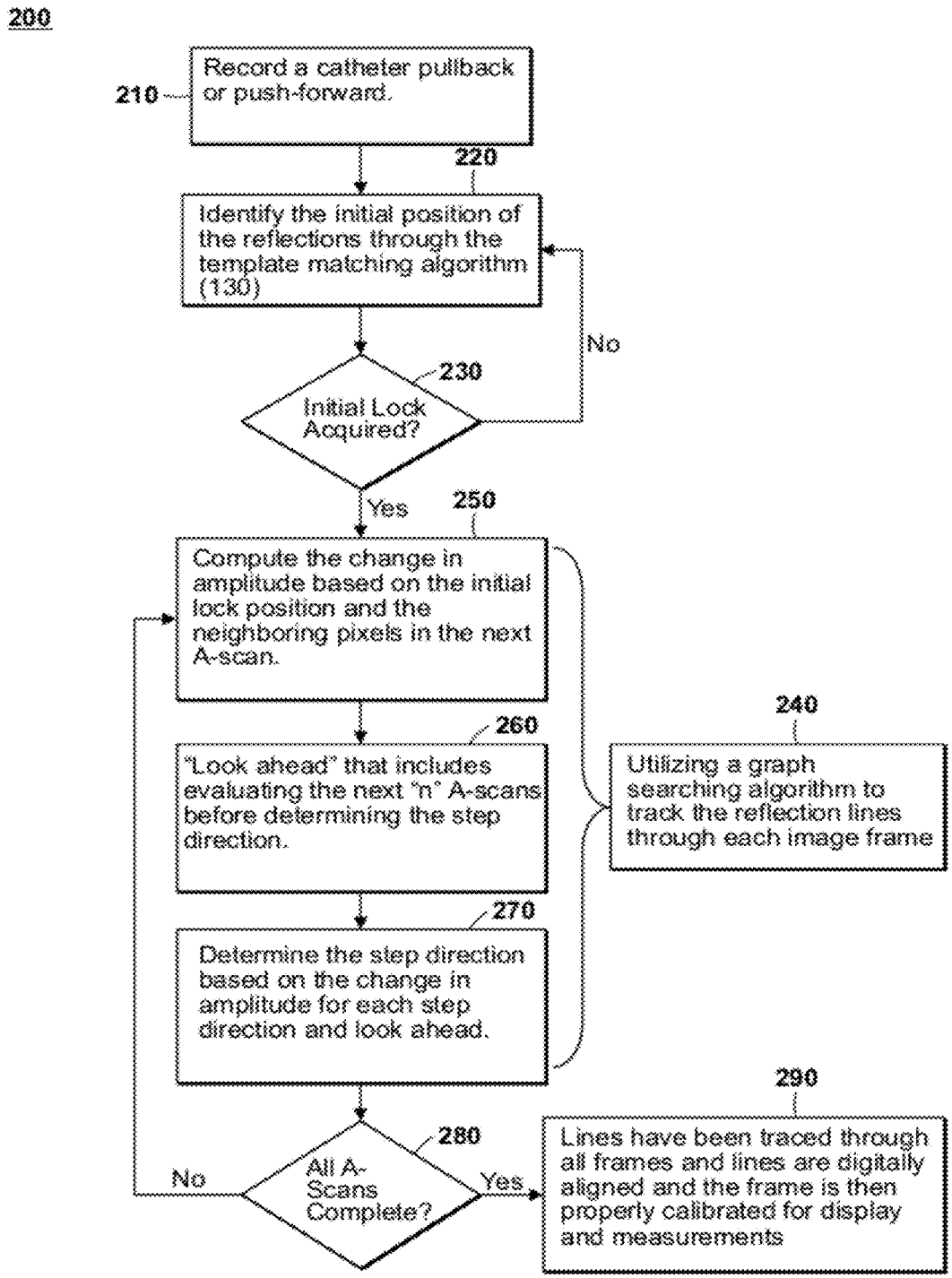
FIG. 9 is a flowchart displaying the second mode of the playback tracking step 200, in accordance with one embodiment.

With reference to FIG. 9, an illustrated method of the second mode and the playback tracking 200 is shown. The playback tracking method 200 begins with step 210 of recording a catheter pullback or push-forward. The objective of the playback mode tracking is to digitally aligning the image data to ensure any shifts to the reflection positions during image acquisition are corrected to allow for proper analysis and/or measurements. Tracking the reflections through the recorded dataset is slightly more difficult due to the motion during pullbacks and the position of the reflections can vary significantly over a single frame. FIG. 3 demonstrates an example of significant shifting of the catheter reflections during a tortuous pullback. The playback tracking method, 200, utilizes a graph searching algorithm to track the reflection through each image frame. Prior to beginning the graph search algorithm in step 220 the initial position of the reflections are identified using the template matching algorithm described 130 above. Once an initial lock 230 is acquired, step 240 tracks the reflection lines through the image based on their amplitude and relative position. In one embodiment, the lines are tracked through the image based on their amplitude and relative position by maintaining a constant distance. Step 250 begins with the first A-scan, then looks at the neighboring pixels in the following A-scan to determine the direction for the next step, and repeated for each A-scan. Step 260 allows for "look ahead" that includes evaluating the next A-scan and looking ahead at the next "n" A-scans before determining the step direction. Step 270 uses the information from steps 250 and 260 to determine the direction of the reflections in the current A-Scan. In 280 the algorithm increments to the next A-Scan and repeats the same processing until all A-Scans in the playback have been evaluated. The black lines tracing the reflection in FIG. 3 demonstrate the results of the graph search algorithm. FIG. 4 provides a slightly more detailed explanation of the graph search algorithm. Step 290 traces the reflection lines through an entire frame they are digitally aligned and the frame is then properly calibrated for display and measurements.

Figure 10:
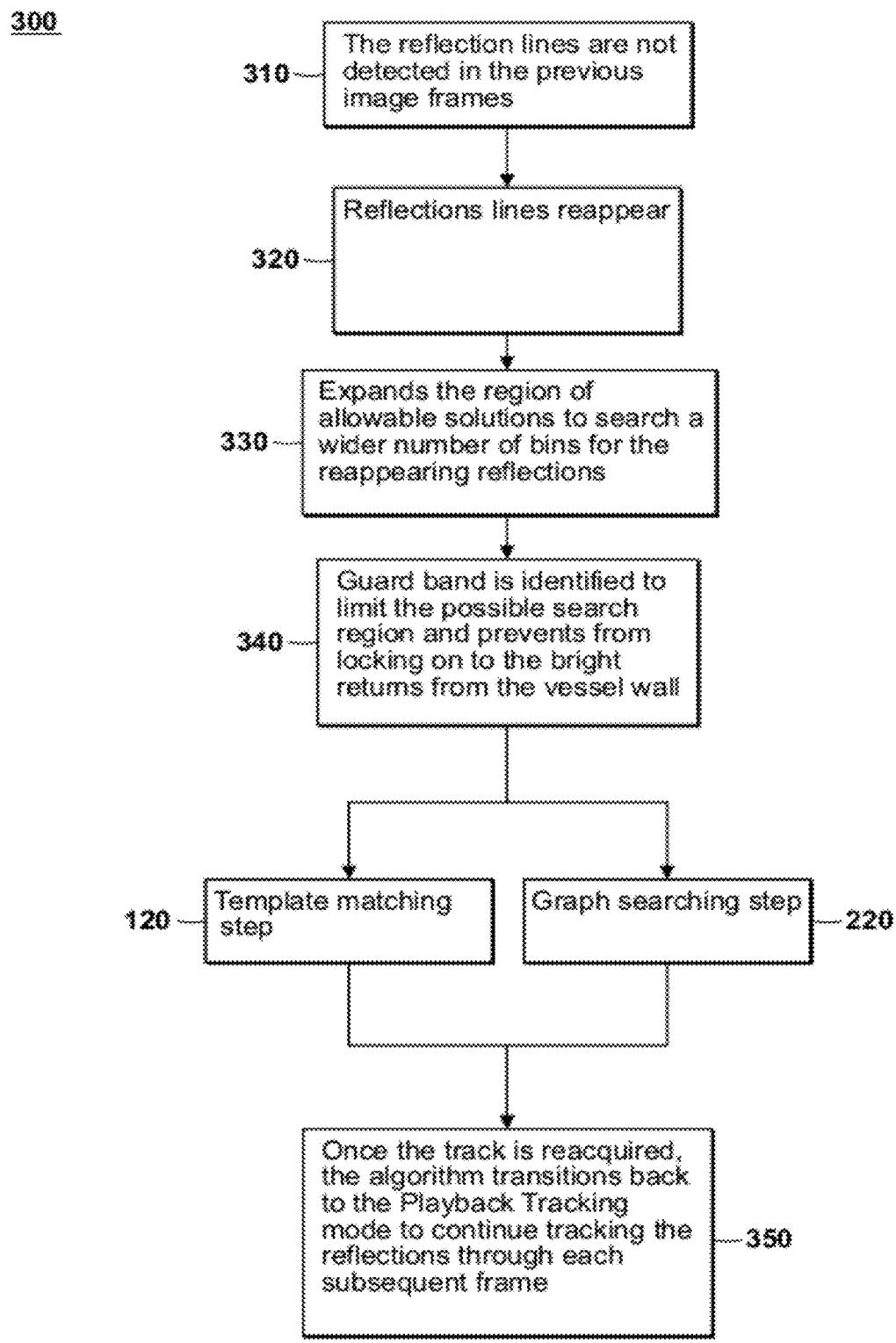
FIG. 10 is a flowchart displaying the third mode of the reacquiring lost track step 300, in accordance with one embodiment.

With reference to FIG. 10, an illustrated method of the third mode and the reacquiring lost track method 300 are shown. The reacquiring lost track method 300 begins at step 310 if the reflection lines are not detected in the previous image frames. In one embodiment, the reflection lines may be lost during a tortuous pullback of the catheter. Once the reflections reappear at step 320, the lost track may be reacquired with the graph search step 220 and the template matching algorithms 120, as indicated above. The graph search step 220 expands the region of allowable solutions to search a wider number of bins for the reappearing reflections in step 330. In step 340, the "guard band" is identified to limit the possible search region and then locking on to the bright returns from the vessel wall is prevented. The template matching step 120 may also be performed as described in the Initial Locking step above. In step 350, once the track is reacquired, the algorithm transitions back to the Playback Tracking mode to continue tracking the reflections through each subsequent frame.

Figure 11:
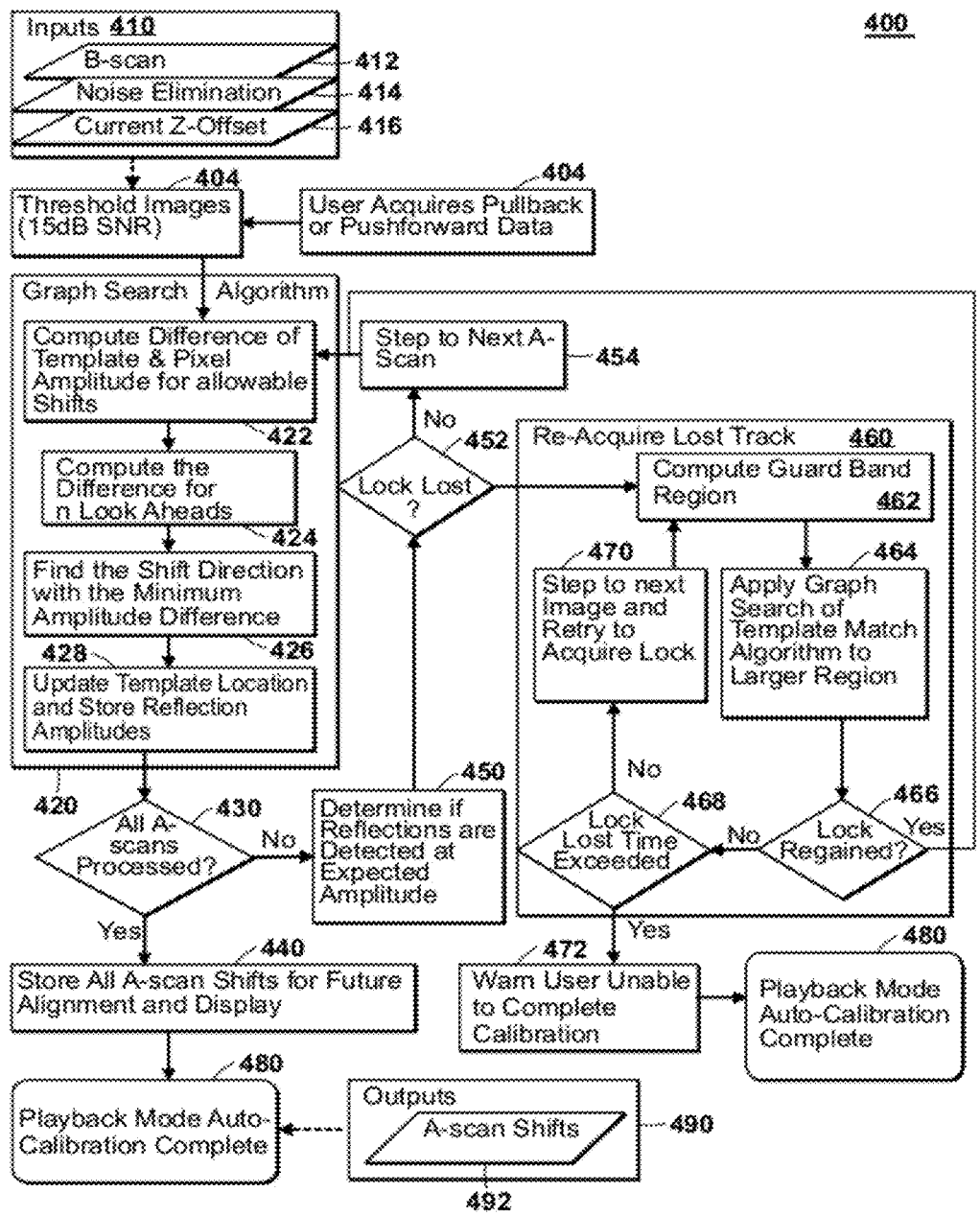
FIG. 11 is a flowchart displaying the auto-calibration in playback method 400, in accordance with one embodiment.

With reference to FIG. 11, an alternative embodiment of the auto-calibration in playback method 400 is shown. The method 400 generally comprises acquiring pullback or push-forward data 402 and obtaining a threshold image 404. A number of inputs 410 may be coupled to the threshold image, such as B-Scan data 412, noise estimates 414, or current Z-offset 416. Next, step 420 is the graph search algorithm 420, which includes computing the difference of template and pixel amplitude for allowable shifts 422, computing the difference for n-look aheads 424, finding the shift direction with the minimum amplitude difference 426, and updating the template location and storing the reflection amplitudes 428. Next, decision 430 determines if all A-scans have been processed. If so, the method proceeds to step 440 in storing all A-scan shifts for future alignment and display, and then playback method for autocalibration is complete 480. A further output 490 may include the data of the A-scan shift 492 for the playback method 400. If all the A-scans have not been processed at decision 430, then step 450 is determining if reflections are detected at an expected amplitude value. Decision 452 determines if the lock is lost. If the lock is not lost, the step 454 proceeds to step to the next A-scan and to the Graph Search algorithm 420 and step 422 of computing the difference of template and pixel amplitude values for allowable shifts. If the lock is lost, then the Re-Acquire the lost track step 460 is implemented. The Re-Acquire lost track step 460 begins with step 462 of computing the guard band region, then applying the graph search step of the template matching algorithm to the larger region in step 464, as described previously. Next, decision 466 determines if the lock has been regained. If the lock has been regained, then the Graph Search algorithm 420 is initiated and the step 422 of computing the difference of template and pixel amplitude values for allowable shifts. If the lock has not been regained, decision 468 determines if the lock lost time has been exceeded. If the lock lost time has been exceeded, the step 472 warns the user that calibration is unable to be completed, and the playback method of the auto-calibration is complete in step 480 to be reinstituted or adjusted by the user. If the lock lost time has not been exceeded, step 470 steps to the next image and retries to acquire the lock and proceeds to step 462 to compute the guard band region once again in the Re-Acquire track step 460.

Figure 12:
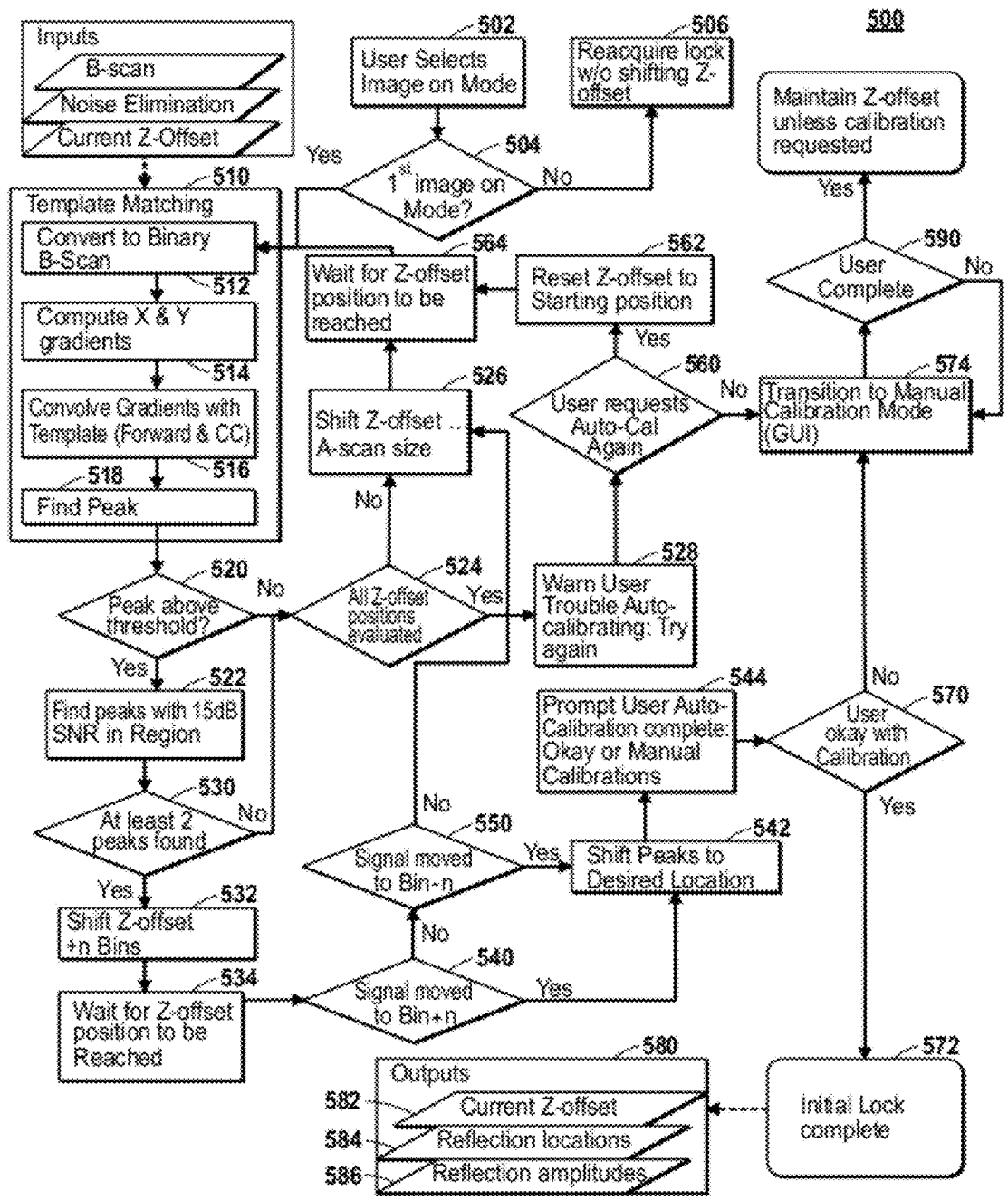
FIG. 12 is a flowchart displaying the auto-calibration initial lock method 500, in accordance with one embodiment.
Figure 13A:
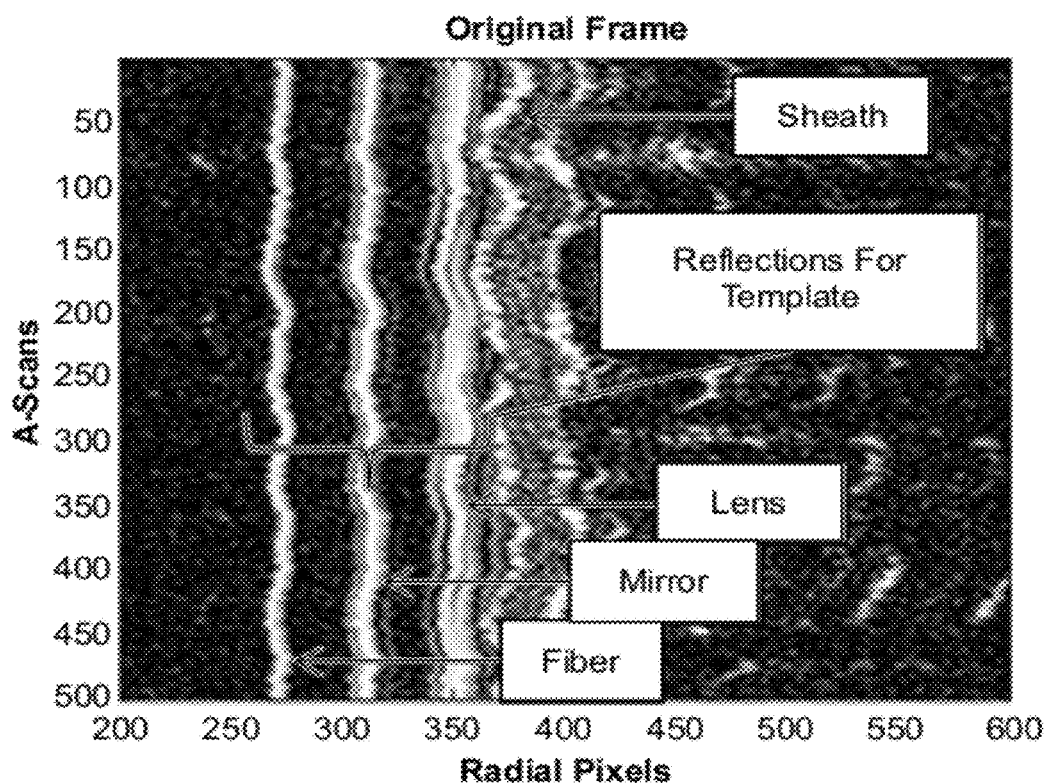
FIGS. 13A-13D are graphs of the first step in the initial lock mode of searching for a strong reflection using the mean amplitude or gradients and adjusting the Z-Offset until detected.
Figure 13B:
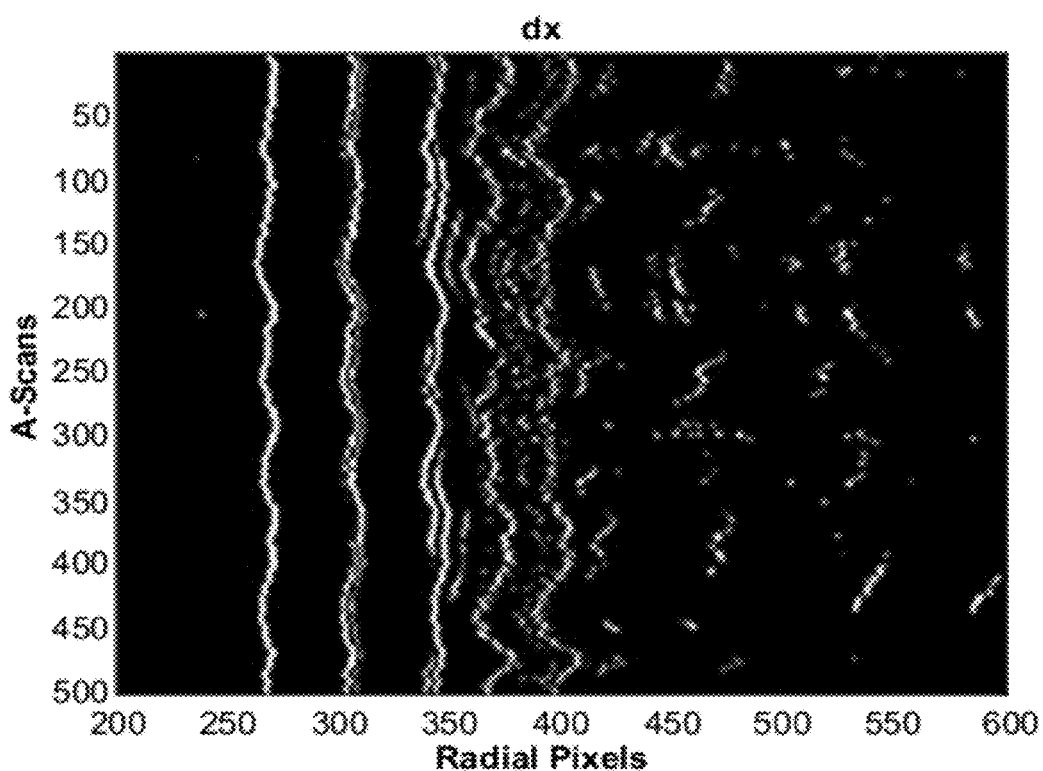
Figure 13C:
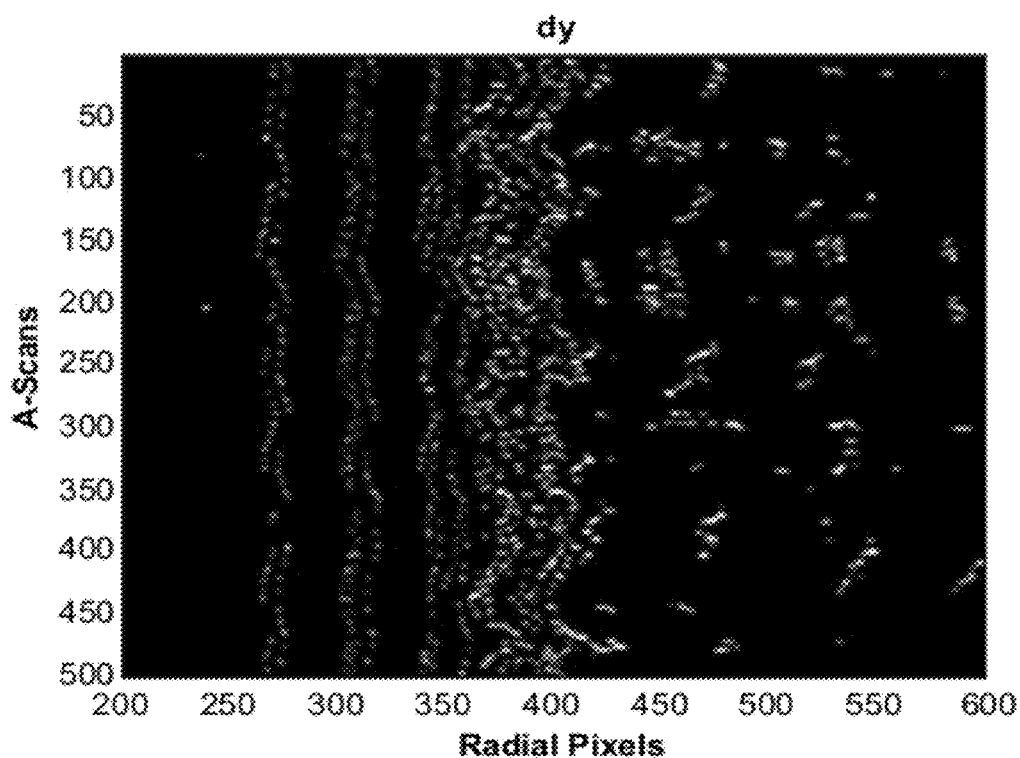
Figure 13D:
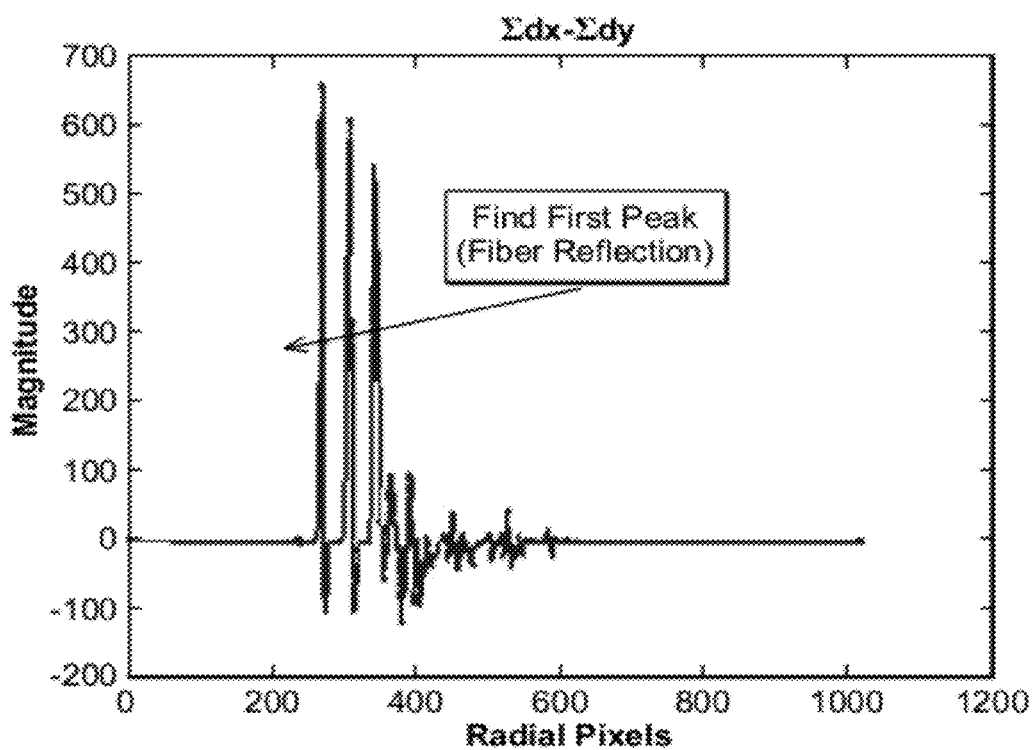

With reference to FIG. 12, an alternative embodiment of the auto-calibration initial lock method 500 is shown. The method 500 generally comprises selecting an image on mode and proceeds to decision 504 to determine whether the first image is on mode. If it is not the first instance of the image on mode for a catheter, step 506 proceeds in reacquiring the lock without shifting the Z-offset position. If it is the first instance of the image on mode, then the template matching step 510, as described above. The template matching step 501 starts with step 512 of converting the image to a binary B-scan, proceeds to step 514 of computing the X and Y gradients, proceeds to step 516 convolving the gradients with the template (Forward and CC), and finds the peak 518 at step 518. The template matching step 510 is finished and proceeds to decision 520 to determine if the peak threshold is obtained. If the peak threshold is obtained, then step 522 finds the peak with a signal-to-noise ratio threshold in the region. If the peak threshold is not obtained, then decision 524 determines if the all the Z-offset positions have been evaluated. Step 522 proceeds to decision 530 to determine if at least 2 peaks have been found. If at least two peaks have not been found, then decision 524 is initiated. If at least two peaks have been found, then step 532 shifts the Z-offset to +n Bins. Then step 534 waits for the Z-offset position to be reached and proceeds to decision 540. Decision 540 determines if the signal is moved to Bin +n. If the signal is moved to Bin +n, the step 542 shifts the peaks to the desired location. If the signal is not move to Bin +n, the Decision 550 determines if the signal is moved to Bin −n. If the signal is moved to Bin −n, then it proceeds to step 542. If the signal is not moved to Bin −n, then it proceeds to Decision step 526 to shift the Z-offset ¼ of the A-scan size. Decision 524 also shifts to step 526 if all the Z-offset positions have not been evaluated. If all the Z-offset position have been evaluated, then step 528 warns the user that there is trouble in the auto-calibration and to try initiation of the method 500 again. Then step 528 proceeds to Decision 560 to determine if the user is requesting the auto-calibration method again. If the user is requesting the auto-calibration method again, then step 562 resets the Z-offset to the starting position. Step 562 then proceeds to step 564 to wait for the Z-offset position to be reached, which then proceeds to the template matching step 510 and step 512 of converting the image to a binary B-scan.

Step 542 proceeds to step 544 to prompt the user that auto-calibration is complete for entry of manual calibrations or accepting the auto-calibration. Step 544 then proceeds to decision 570, which determines if the user is okay with the calibration. If the user accepts the calibration, then the initial lock method is complete in step 572. The outputs 580 for the initial lock include the current Z-offset 532, the reflection locations 584, or the reflection amplitudes 586. If the user does not accept the calibration, then step 574 transitions to manual calibration mode through a Graphical User Interface (GUI). Then decision 590 allows the user to complete the calibration. If the user completes the calibration, then step 592 maintains the Z-offset unless calibration is further requested. If the user does not complete the calibration, the step 574 transitions to manual calibration mode for additional attempts by the user.

Automatic Calibration of Z-offset Method 3: Auto-Template Generation and Full Correlation. Alternatively, the template may not be stored on a memory chip or the RFID, as in the previous Method 2, and the template may be automatically generated during an initial lock mode process, as described below for Method 3. The previous method utilized a binary template for template matching, while Method 3 generates a template with amplitude information and the complex conjugate signal information. Utilizing amplitude information and generating the minor signal increases the likelihood of locking on to the correct reflection lines. Additionally, Method 3 step or algorithm performs Auto-Calibration during initial lock and playback mode, and Method 3 also maintains calibration during a live mode (when the catheter is imaging but is not recording data).

In one embodiment for the first mode is the initial lock, which utilizes the internal catheter reflections (fiber, minor and lens) to identify the required VDL shift to reach the calibration position, as described in previous methods. The initial lock Z-Offset calibration is the step in which the reflection pattern or the template is determined. The template identified in the initial Z-offset calibration is utilized in each subsequent calibration mode to track the shift of the reflections and apply the analog and digital shifts, as required or implemented. The template region is identified using gradient and amplitude information. Once the template is identified and stored for later use, the VDL shift is applied and the catheter is ready for calibration during live and playback mode. Acceptable error in this position will be determined by the ability of the next mode (maintenance of Z-offset during live imaging) to lock onto the reference pattern of catheter reflection lines in the OCT image.

FIGS. 13-16 provide an overview of the alternative steps for the initial Z-Offset calibration. FIGS. 13A-13D are graphs of the first step in the initial lock mode of searching for a strong reflection using the mean amplitude or gradients and adjusting the Z-Offset until detected. FIG. 13A shows that there are reflections present for the fiber, mirror, lens, sheath, and reflections for the template. The algorithm utilizes X and Y gradients of the image to determine if reflections are present. FIG. 13B is the change of the X gradient and FIG. 13C is the change of the Y gradient. If no reflections are found, the VDL is shifted to the next possible Z-offset location. Once strong reflections are identified, a slight positive VDL shift is applied to verify the orientation of reflections. If the reflections shift towards the center of the image, then the reflections are oriented properly for calibration. If the reflections shift outward, the image is the complex conjugate signal and a large negative VDL shift is applied to unwrap the image. After the image is determined to be properly oriented, the reflections are shifted to the center of the window to ensure the full template region is visible. If at any point during each of the shifting steps the reflection lines are no longer detected, the algorithm applies a new Z-offset and starts over looking for strong returns. FIG. 17 provides a more detailed version of the algorithm and user interaction.

Figure 14A:
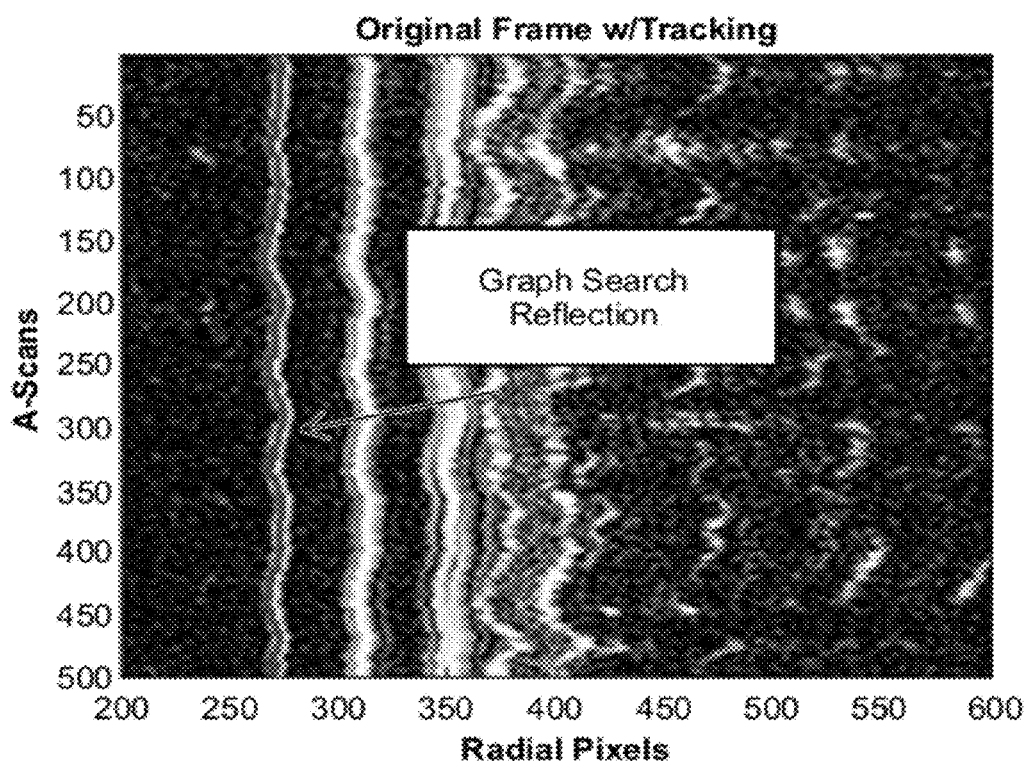
FIGS. 14A-14B are graphs of the second step in the initial lock mode of aligning the reflections across the A-scans in the rectangular image.
Figure 14B:
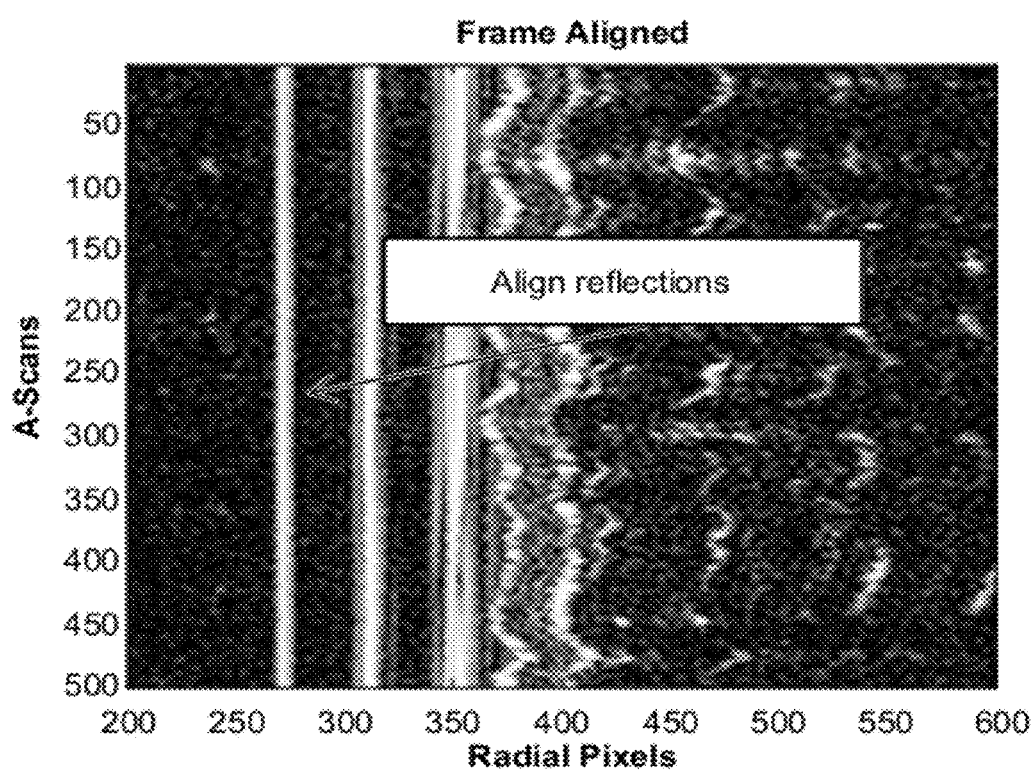

Once the reflections have been centered in the image window the template is computed. The template is an array of pixel numbers versus average amplitude values beginning at the fiber reflection and ending at the lens reflection. The first step in identifying the template is to align the image based on the first strong reflection using a simple graph search algorithm, as shown in FIG. 14A. Aligning the reflections across the A-scans is in the rectangular image is the second step for the initial lock Z-offset calibration mode. Image alignment is done to increase the likelihood reflections are straight in the rectangular image and will be easily identified by their gradients and amplitude, as shown in FIG. 14B. Once the image alignment is complete, the internal catheter reflections are identified using 4 characteristics: (1) Strong X and Weak Y Gradients (Assuming A-Scans Along the Y axis); (2) Consistently High Signal-to-Noise Ratio (SNR) of at least greater than 15 dB; (3) Maximum Distance from First Reflection (Fiber) to Last Reflection (Lens); and (4) Minimum of at least 2 Reflections.

Figure 15A:
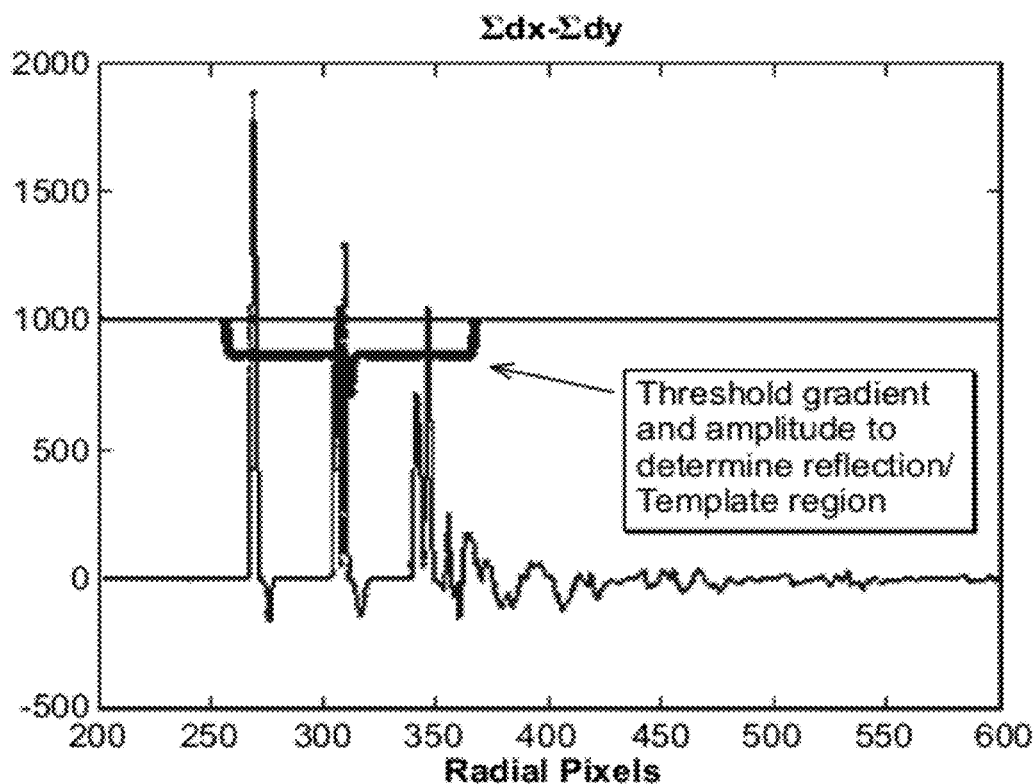
FIGS. 15A-15B are graphs of the third step of identifying the catheter reflections using the gradient and amplitude.
Figure 15B:
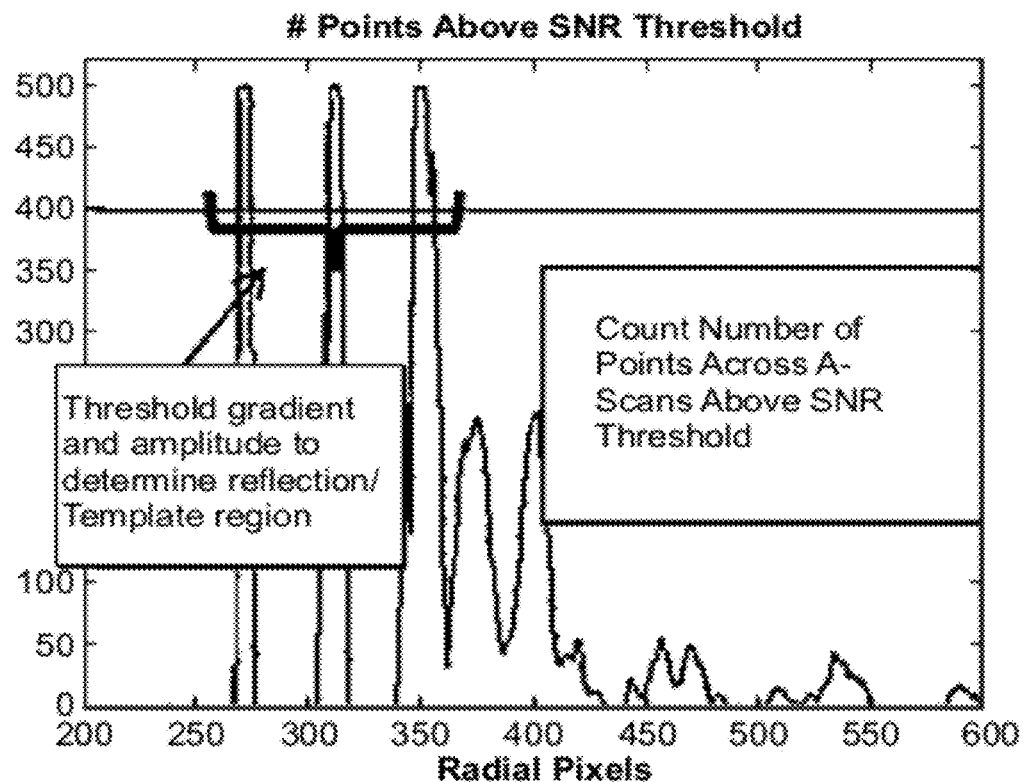
Figure 16A:
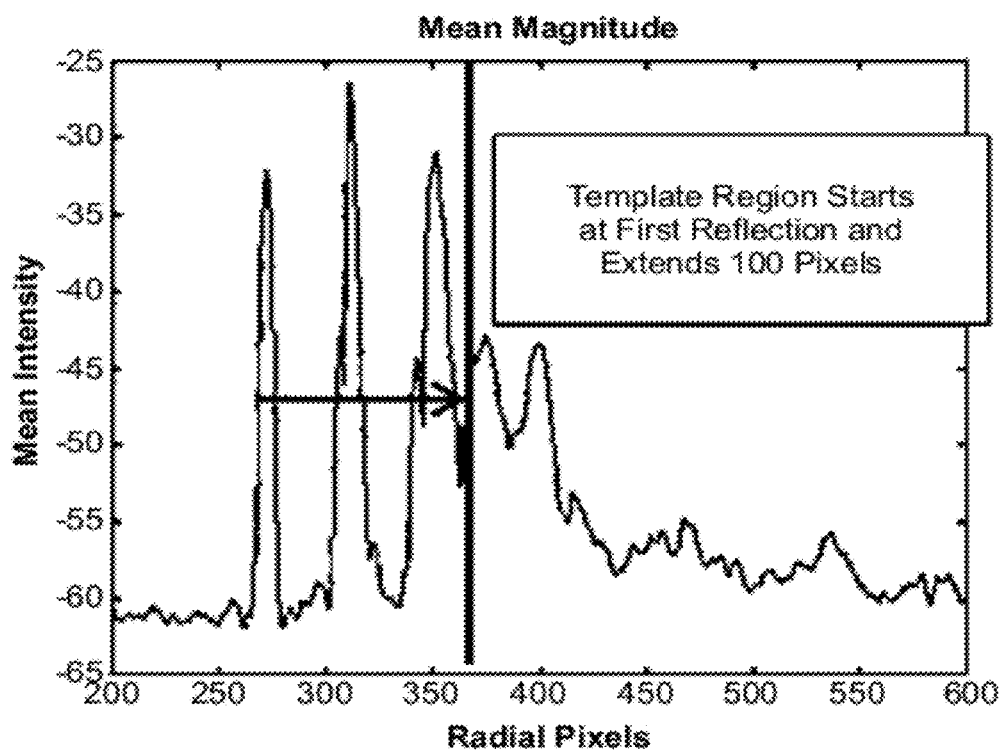
FIGS. 16A-16B are graphs of the fourth step in the initial lock mode of generating the template of reflections and storing for later use.

As shown in FIGS. 15A-15B, the third step in the initial lock mode is to identify the catheter reflections using the X and Y gradients. Step 4 of the initial lock generates template of reflections and stores the template for later use. The template region is then defined as the mean across A-Scans (i.e. angular) starting from the first reflection and ending at the last reflection (with a 5 pixel margin on either side), as shown in FIG. 16A. To prevent small templates due to weak lens reflection, the minimum template size is 100 bins. Alternatively, the minimum template size is at least between about 20 and 1000 bins. Therefore, if the Lens reflection is not detected, the 100 bins after the fiber reflection are selected as the template region. This minimum distance threshold may be determined based on the minimum distance from the fiber to the Inner Diameter (ID) of the sheath. The accuracy of the template is highly dependent on locating the fiber reflection. If the fiber reflection is not found, the template may include the sheath or vessel region and result in improper calibration.

Figure 16B:
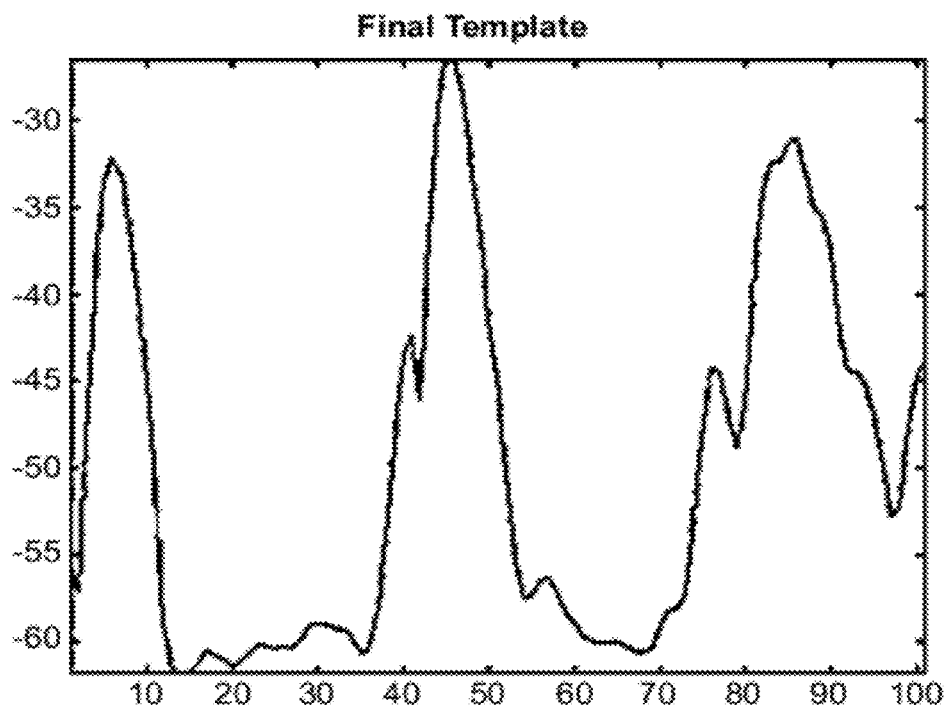
Figure 17:
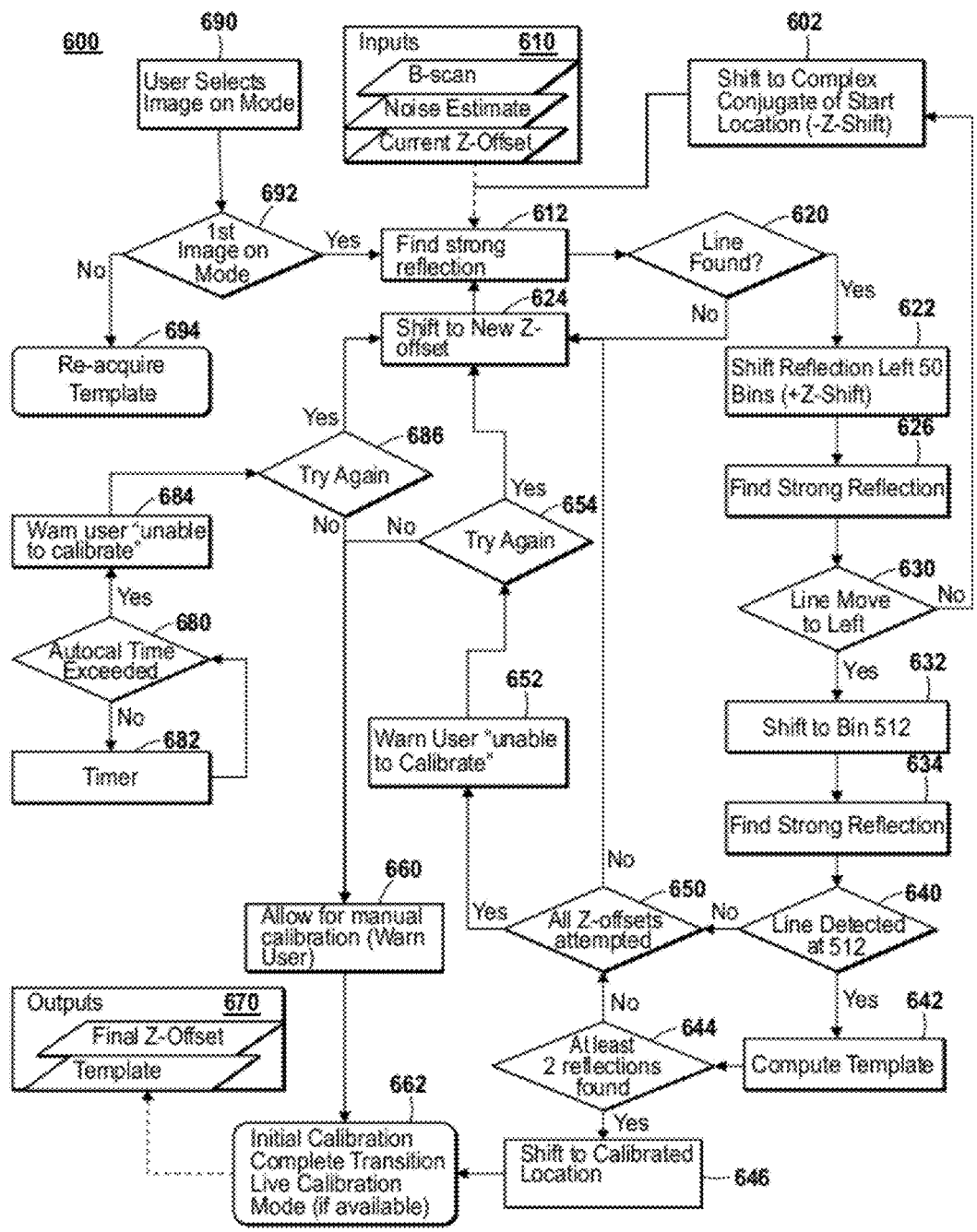
FIG. 17 is flow chart of the Initial Z-Offset Calibration.

As shown in FIG. 16B, once the template is found, it is stored for later use in the subsequent auto-calibration algorithms. The VDL is then shifted to position the fiber reflection at a pre-determined location and the system transitions to live mode. If the reference pattern is not found at this initial VDL position (unlikely but still non-zero probability), the value is assumed to be incorrect and a backup initial estimate search is performed by the system. The backup search procedure sweeps through VDL positions in a pre-determined fashion while the pattern recognition algorithm attempts to lock onto the reference pattern. Entering this backup search procedure is undesirable, because additional time is used to find the correct initial calibration. If the backup search fails (i.e. is unable to lock onto the reference pattern), the system assumes that the catheter or its connection to the PIM is faulty and the user is notified to use an alternate catheter.

FIG. 17 is flow chart of the Initial Lock Z-Offset Calibration method 600. The first step is 690 where the user selects the image on mode. If this is the first image on mode, decision 692, the algorithm proceeds to 612 searching for a strong reflection. Various inputs 610 such as the B-Scan, noise estimate, and current Z-offset may be coupled with step 612. If it is not the first image on mode, the algorithm moves to completion box 694 to reacquire the template by simply shifting the VDL to the position the last template was acquired. After step 612, decision 620 determines if a reflection line has been found. If a reflection has been found, the step 622 proceeds to shift the reflection left n-number of bins for a +Z-shift. In one embodiment, the shift of the reflections may be between about 25 to 100 bins. If the reflection has not been found, then step 624 shifts to a new Z-offset. After step 622, step 626 finds a strong reflection meeting a certain threshold using the mean amplitude or gradient, as indicated previously. Then decision 630 determines if the reflection line move has been to the left. If the reflection line has moved, the step 632 shifts to a particular bin number. If the reflection line has not been moved, then step 602 shifts the VDL to the complex conjugate (CC) of the start location (−Z-shift) to reset to find a strong reflection 612. After step 632, step 634 finds the strong reflection and proceeds to decision 640 to determine if the line has been detected at a particular bin. If the line has been detected at a particular bin, then step 642 computes the template. If the line has not been detected, then decision 650 determines if all the Z-offsets have been attempted. If all the Z-offset have not been attempted, then step 624 shifts to a new Z-offset position and step 612 to find the strong reflection. If all the Z-offsets have been attempted, then step 652 warns the user that the program is unable to calibrate. After step 652, decision 654 warns the user to try again. If the user selects to try again, then step 624 shifts to a new Z-offset and step 612 to find the strong reflection. If the user does not select to try again, then step 660 allows for manual calibration and warns user of manual calibration mode. After step 660, results 662 provides for the initial calibration and complete transition of the live calibration mode. Outputs 670 may be provided for the final Z-offset and the template.

After step 642, decision 644 determines if at least two reflections are found. If at least two reflections are found, step 646 shifts to the calibrated location. If at least two reflections are not found, then decision 650 is attempted to determine if all the Z-offsets have been attempted. In one embodiment, a timer 680 may be coupled with the decision 680 to determine if the autocalibration time has been exceeded. If the autocalibration time has been exceeded, then step 684 warns the user that the program is unable to calibrate. After step 684, decision 686 allows the user to try again. If the user selects to try again, the step 624 shifts to a new Z-offset to find a strong reflection. If the user does not select to try again, the step 660 allows for manual calibration.

In an alternative embodiment of the second mode, a live mode tracking step may be employed. During live mode auto-calibration, the template computed during the initial lock step is utilized to maintain the initial lock calibration position for all frames displayed on the screen on a video monitor or other display device. In one embodiment, the initial lock calibration position for all frames may be at a rate of at least 30 frames-per-second (fps), alternatively, between about 10 to 50 fps. The catheter system may become un-calibrated due to shifts in the optical path length caused by changes in temperature when the catheter is inserted into the body or mechanical strain on the fiber when the catheter is longitudinally pushed or pulled. The live mode algorithm detects the position of the catheter reflections using the template and updates the digital and analog calibration settings to maintain the proper calibration setting. If only a small shift is necessary to maintain the calibration position, a digital shift is applied to the image prior to display. However, if the system becomes significantly un-calibrated or a large shift is necessary to maintain calibration, a Z-offset update is applied (VDL shift).

Figure 18A:
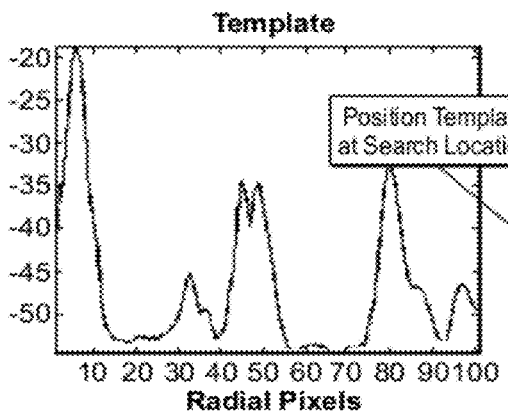
FIGS. 18A-18D are graphs of the first step in the live tracking mode shifting the template to search the location and creating the "Full Template" with a mirrored signal.
Figure 18B:
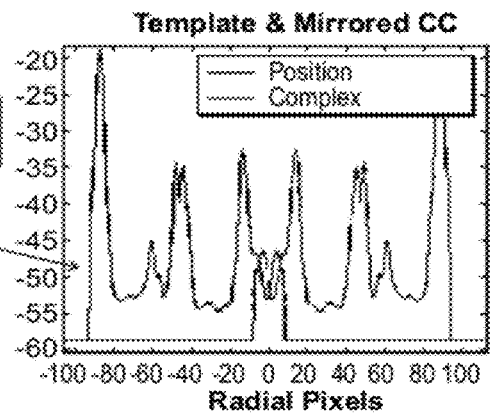
Figure 18C:
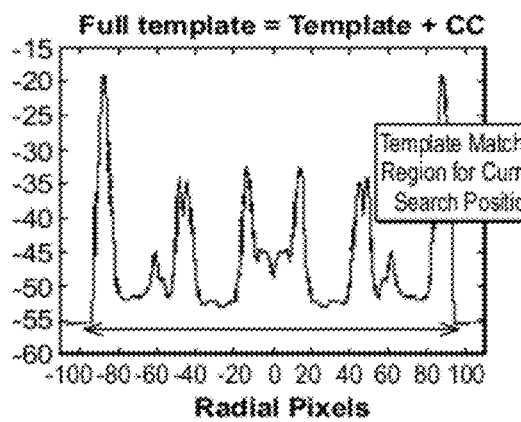
Figure 18D:
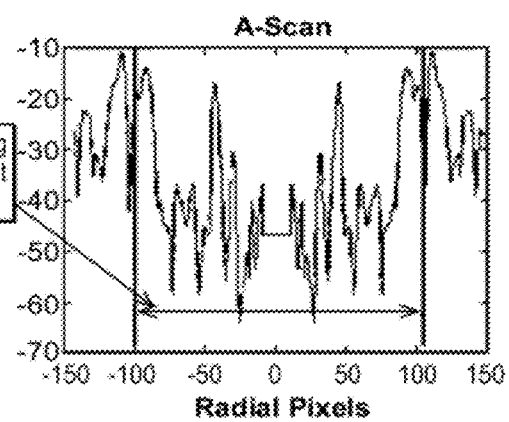
Figure 19:
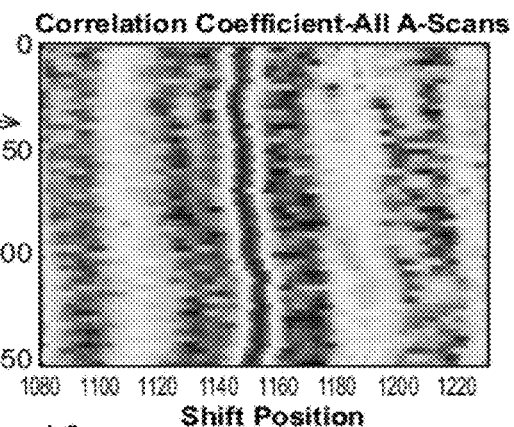
FIG. 19 is a graph and equation for the second step in the live tracking mode for computing the correlation coefficient for the template and all A-scans, which is limited to template size.

The reflections are identified during live-mode tracking by finding the maximum correlation between the template and A-scans (i.e. template matching). The search region for identifying the reflections is limited based on the maximum expected shift from frame to frame. The template matching algorithm is slightly different than most standard template matching implementations, since it modifies the template based on the search position to account for the wrapped complex conjugate signal. Prior to computing the correlation, the "full template" is generated which includes the mirrored complex conjugate signal, as shown in FIGS. 18A-18D. To compute the full template, first the original template is shifted to a search position, as shown in FIG. 18A, and second the signal is summed with the mirrored version of the same signal, as shown in FIG. 18B. The correlation coefficient of the full template and each A-scan is then computed, as shown in FIG. 19. This process is then repeated for each possible shift position in the search region. Once all correlations have been computed, the position of maximum correlation for each A-scan is found, as shown in FIG. 20. The final reflection position is assigned as the median position of the top "n" correlations. Once the calibration shift is identified, the image is digitally adjusted to return the reflections to their calibrated position, as shown in FIGS. 21A-21B. If the shift is beyond a pre-determine threshold for "n" frames, an update to the Z-offset (VDL) is applied. This algorithm is repeated for every image displayed on a screen in live mode and utilizes the previous frames correlation match and Z-offset to determine the search region for the next frame.

Figure 22:
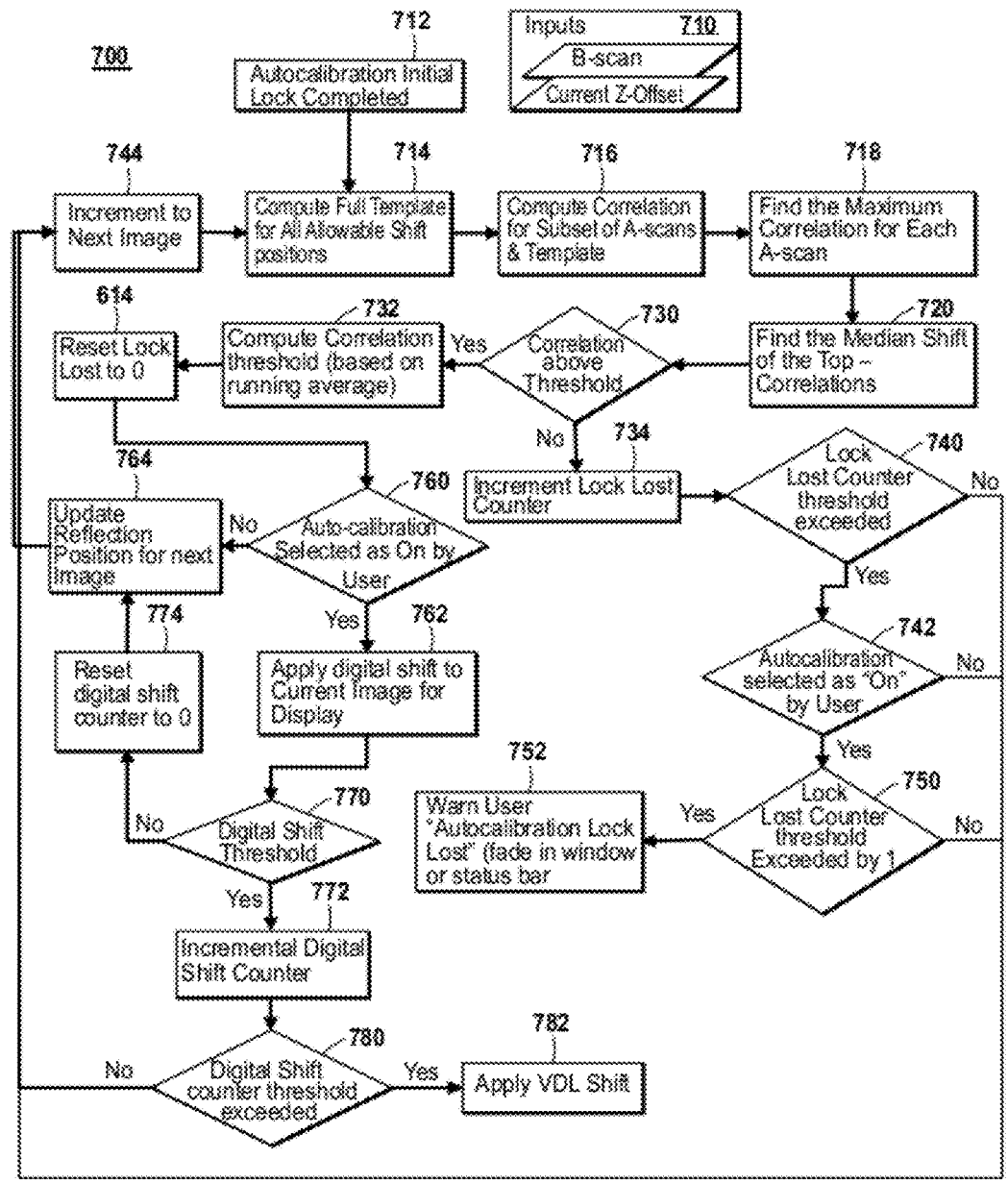
FIG. 22 is a flow chart of the live-mode tracking, in accordance with one embodiment.

FIG. 22 provides a flowchart of the algorithm and the user interaction for the live mode tracking process 700. In the live mode calibration process, the calibration continues until "image off" is selected or a catheter longitudinal pullback is initiated. The position of the reflections just before the pullback begins is stored for use in a Playback Mode autocalibration setting, as described below. Various inputs 710 may be coupled with the live-mode tracking process, such as the B-scan, the current Z-offset, and the like, as previously indicated. Step 712 determines if the autocalibration of the initial lock has been completed. Then step 714 computes the full template for all allowable shift positions. Then step 716 computes the correlation for the subset of A-scans and the template. Then step 718 finds the maximum correlation for each scan. Then step 720 finds the median shift of the top n-correlations. Then decision 730 determines if the correlation is above a particular threshold. If the correlation is above a particular threshold, then step 732 compute the correlation threshold based on the running average. If the correlation is not above a particular threshold, the step 734 incremental lock lost counter proceeds. After step 734, decision 740 determines if the lock lost counter threshold has been exceeded. If the lock lost counter threshold has been exceeded, then decision 742 checks if the user has selected autocalibration as "on" to determine if the user needs to be warned for the error. If the lock lost counter threshold has not been exceeded, then step 744 proceeds to increment to the next image, which is followed by step 714 to compute the full template for all allowable shifts positions for live-mode tracking. In decision 742, if the autocalibration is selected "on" by the user, then decision 750 determines if the lock lost counter threshold is exceeded by 1. If the autocalibration is not selected "on" by the user, the step 744 proceeds to increment to the next image. If the lock lost counter threshold is not exceeded by 1, then step 744 proceeds to increment to the next image. If the lock lost counter threshold is exceeded by 1, then step 752 warns the user that the autocalibration lock was lost, whereby the program can fade in the window or status bar of the computer.

After step 732, step 736 resets the lock lost to 0. Then decision 760 determines if the autocalibration has been selected "on" by the user. If the autocalibration has been selected "on" by the user, then step 762 applies a digital shift to the current image for display. If the autocalibration has not been selected "on" by the user, then step 764 updates the reflection position for the next image. After step 764, step 744 increments the program to the next image. After step 762, decision 770 determines if the digital shift threshold has been met. If the digital shift threshold has been met, the step 772 proceeds with the incremental digital shift counter. If the digital shift threshold has not been met, then step 774 resets the digital shift counter to 0, which then proceeds to step 784 to update the reflection position for the next image. After step 772, decision 780 determines if the digital shift counter threshold has been exceeded. If the digital shift counter threshold has been exceeded, then step 782 applies a VDL shift. If the digital shift counter threshold has not been exceeded, then step 744 increments to the next image for the live mode tracking process. In the live mode calibration process, the calibration continues until "image off" is selected or a catheter longitudinal pullback is initiated. The position of the reflections just before the catheter pullback begins is stored for use in a Playback Mode autocalibration setting, as described below.

Figures 23A, 23B:
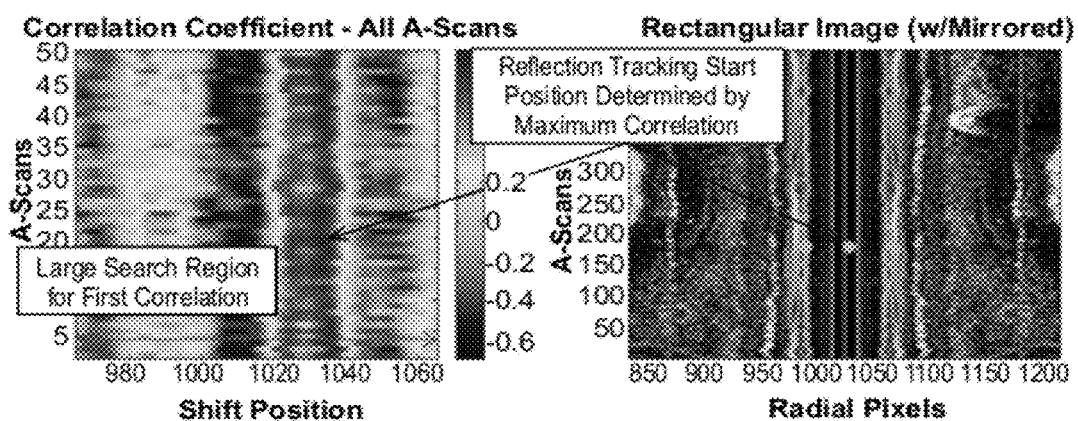
FIGS. 23A-23B are graphs of the first step in the playback tracking mode to determine the starting position of the reflection tracking using maximum correlation across all A-scans with large search region.
Figure 24:
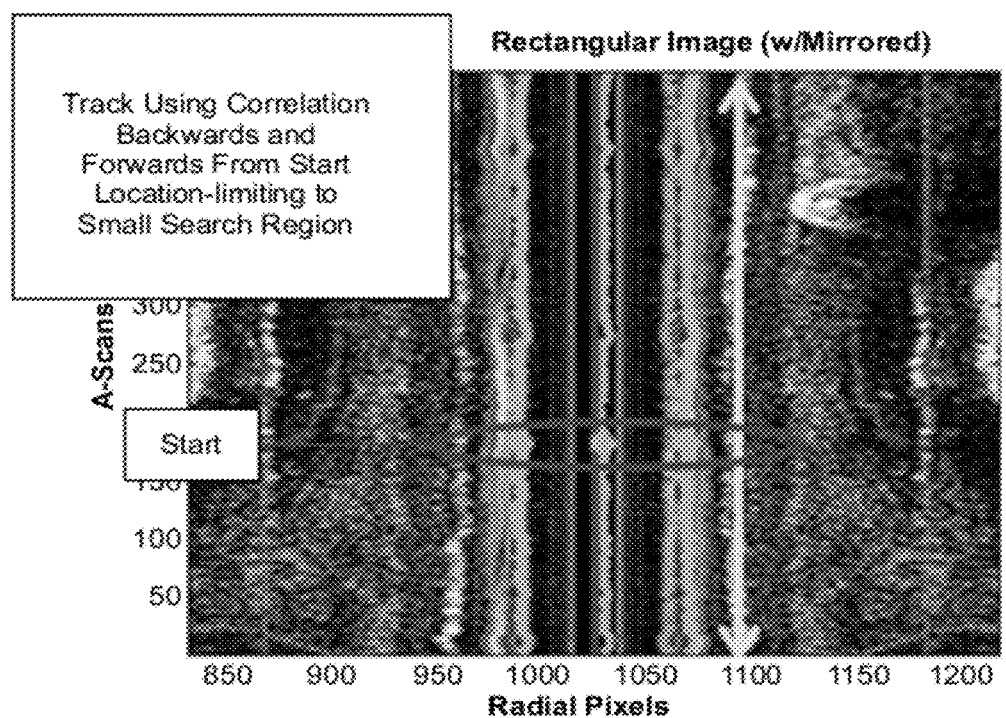
FIG. 24 is a graph of the second step of the playback tracking mode from the starting Position, track reflections backward and forwards A-scan by A-scan using the same correlation technique but with small search region.
Figure 25A:
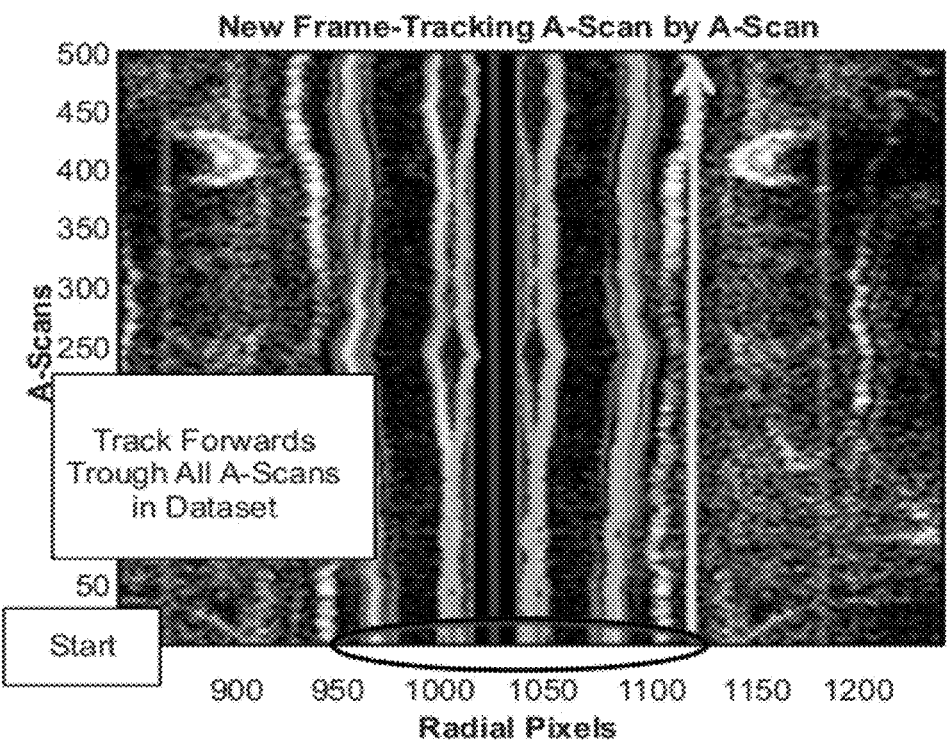
FIGS. 25A-25B are graphs of the third step in the playback tracking mode and continuing to track A-scan by A-scan through all frame in dataset and store reflection position for later alignment and display to a viewer on a video monitor or other physical display device.
Figure 25B:
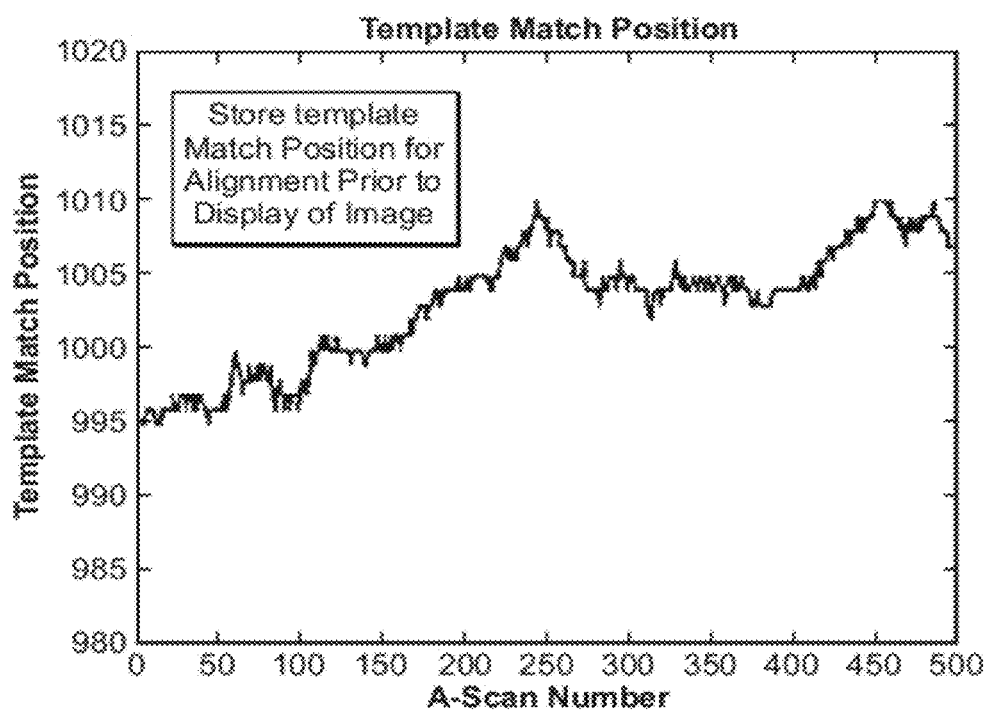

In an alternative embodiment of the third mode, a playback mode tracking occurs after the user has recorded an image dataset. The playback mode tracking performs autocalibration on every A-scan in the dataset. Similar to live mode tracking, the playback mode utilizes the correlation of the template and image A-scans at limited shift locations to determine the position of the reflections. Identifying the initial position of the reflections is such that the first frame of the dataset is treated different from the other frames. In the first frame of the dataset, the correlations for all allowable shifts and all A-scans are computed to find the maximum correlation, as shown in FIGS. 23A-23B. From the point of the maximum correlation, the algorithm then traces through each A-scan backwards and forwards computing the correlation for each possible shift, as shown in FIG. 24. The allowable shift region for the first search is broad to allow for sudden jumps that may occur during the transition from live mode to playback mode. Once the start position is determined, the A-scan by A-scan search is limited to a small region given that the time and possible movement between A-scans is small relative to the frame to frame motion. For example, for the first frame the search region may be set to −50 to +50 pixels from the last location, once the maximum correlation is found, the search region is limited to −1 to +1 pixels for each A-scan. Alternatively, the search region may be set to at least about −500 to +500 pixels, alternatively between at least about −400 to +400, alternatively between about −300 to +300, and the like. The search region may be limited to between about −10 to +10, alternatively, between about −5 to +5, alternatively between about −0.1 and +0.1. Once the first frame has been fully traced, as shown in FIG. 25A, the algorithm moves on to the next frame beginning with the first A-scan and limited the search region based on the position of the reflection in the last A-scan. FIG. 25B shows that the reflection position is stored for later alignment and display through storing the template match position for alignment prior to the display of the image on a screen of a video monitor or other display device. This is repeated for each A-scan in all frames.

Figure 26:
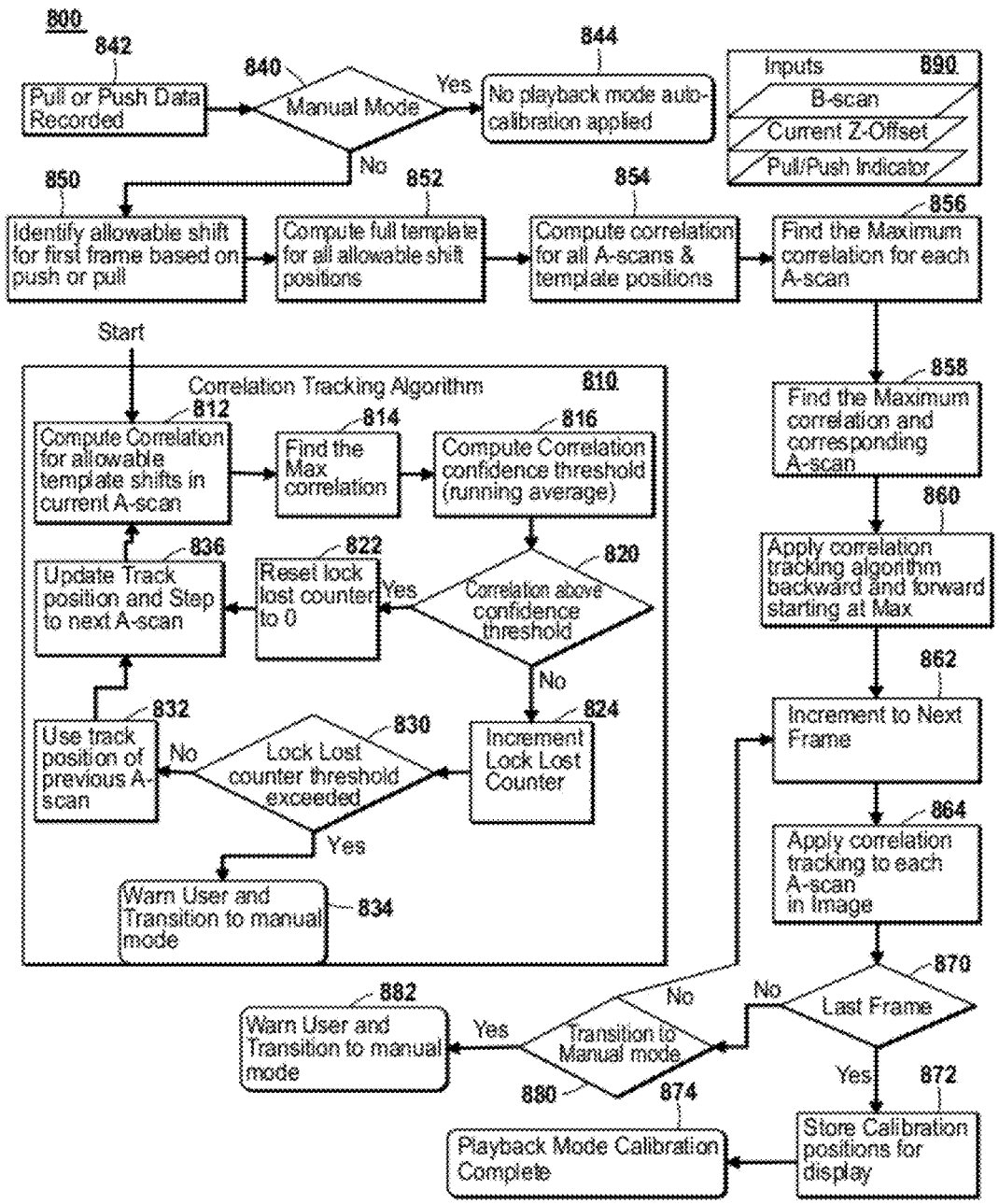
FIG. 26 is a flow chart of the Playback Mode Tracking Algorithm.

The detailed flow chart of the playback mode calibration process 800 is provided in FIG. 26. The playback mode calibration initializes by searching all A-scans within an image to identify the peak correlation. From the peak, the correlation tracker tracks forwards and backwards to identify the reflection position for each A-scan in the first frame. This search is applied to the first frame to guarantee a strong initial lock. Each of the following frames after the first frame is tracked A-scan by A-scan with limited search regions. The manual mode 840 is transitioned when the lock lost counter threshold has been exceeded and the user selects manual mode. Alternatively, the manual mode 840 may be selected if the pull or push data has been recorded 842. If manual mode has been selected, then no playback mode autocalibration will be applied in step 844. If manual mode has not been selected, then step 850 identifies the allowable shifts for the first frame based on the push or pull of the catheter. Then step 852 computes the full template for all allowable shift positions. Then step 854 computes the correlation for all A-scans and template positions. Then step 856 finds the maximum correlation for each A-scan. Then step 858 finds the maximum correlation and corresponding A-scan. Then step 860 applies the correlation tracking algorithm 810 to each A-scan in the image.

The correlation tracking algorithm 810 starts with step 812 of computing the correlation for allowable template shifts in the current A-scan. Then step 814 finds the maximum correlation for that A-scan. Then step 816 computes the correlation confidence threshold of the running average. Then decision 820 determines if the correlation is above a particular confidence threshold. If the correlation is above a particular confidence threshold, then step 822 resets the lock lost counter to 0. If the correlation is not above a particular confidence threshold, then step 824 proceeds to increment the lock lost counter. After step 824, decision 830 determines if the lock lost counter threshold has been exceeded. If the lock lost counter threshold has not been exceeded, the step 832 uses the track position of the previous A-scan. If the lock lost counter threshold has been exceeded, then step 834 it warns the user and transitions to manual mode. Both step 822 and 832 proceed to step 836 to update the track position and steps to the next A-scan. After step 836, step 812 computes the correlation for allowable shifts in the current A-scan.

After step 864 of applying the correlation tracking algorithm to each A-scan in the image, decision 870 determines if it is the last frame. If it is the last frame, then step 872 stores the calibration positions for the display. If there are more frames, then decision 880 determines if the transition to manual mode is required or commanded. If the transition to manual mode has been selected, then step 862 increments to the next frame. If the transition to manual mode has not been selected, then step 882 warns the use and transitions to manual mode. After step 872, step 874 determines that the playback mode calibration has been completed. Various inputs 890 may be coupled with the playback mode process, such as the B-scan, current Z-offset, and the pull or push indicator for the catheter.

Figure 27:
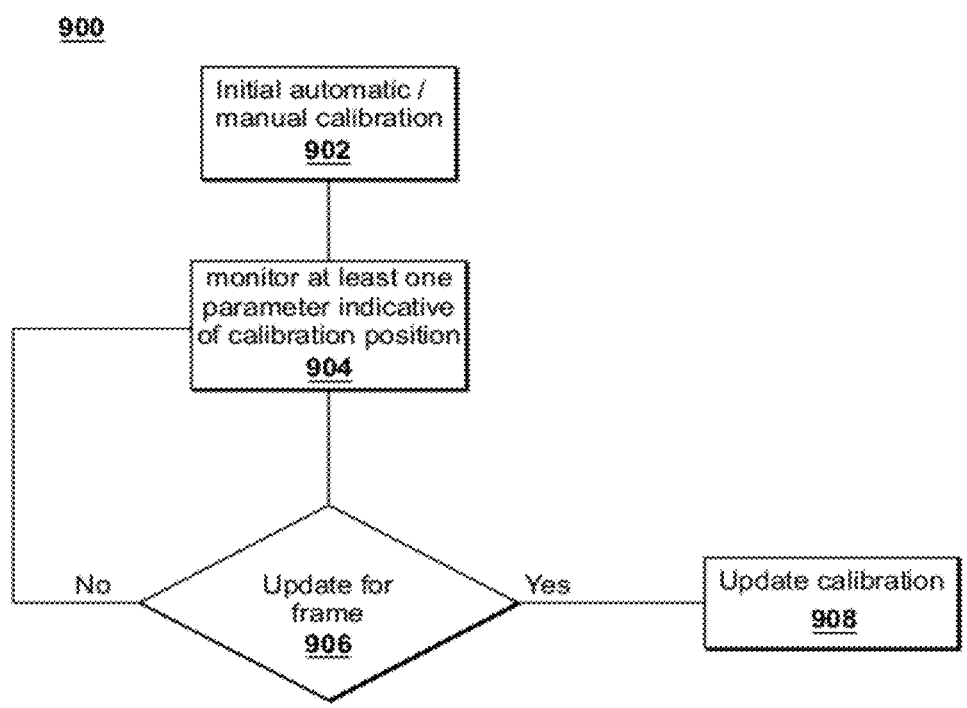
FIG. 27 is a flow chart of one embodiment of the automatic calibration.

Generally, in one embodiment for the auto-calibration 900 is shown in FIG. 27. Any of the previously discussed calibration methods may be used to continuously update and maintain the calibration on a frame-by-frame basis after the initial calibration. Step 902 performs the initial automatic calibration or manual calibration as previously discussed. Step 904 monitors at least one parameter indicative of the calibration position. Decision 906 determines if the calibration needs to be updated on the existing frame or subsequent frame. If the calibration does not need to be updated for the frame, then the automatic calibration continues to monitor the parameter indicative of the calibration position in step 904. If the calibration does need to be updated for the frame, the step 908 automatically updates the calibration (such as to digitally shift the image, apply the z-offset shift, or any of the methods previously discussed. The frame may be an A-scan, or set of frames.

It will be understood that each block of the flowchart illustrations, and combinations of blocks in the flowchart illustrations, as well any portion of the module, systems and methods disclosed herein, can be implemented by computer program instructions. These program instructions may be provided to a processor to produce a machine, such that the instructions, which execute on the processor, create means for implementing the actions specified in the flowchart block or blocks or described for the tissue classifier, imager, control module, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes or even in a different sequence than illustrated without departing from the scope or spirit of the invention.

The computer program instructions can be, stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

It will be understood that the catheter pullback may be performed by pulling the catheter from a proximal end to a distal end of the region being imaged. It also will be understood that the intravascular imaging techniques described above can also be used with other types of imaging techniques that use a catheter insertable into patient vasculature. For example, the intravascular imaging techniques can be used with any imaging techniques configured and arranged to assess one or more measurable characteristics of patient tissue (e.g., intravascular magnetic resonance imaging, spectroscopy, temperature mapping, or the like).

The systems and methods described herein may be embodied in many different forms and should not be construed as limited to the embodiments set forth herein. Accordingly, the disclosed systems and methods may take the form of an entirely hardware embodiment, an entirely software embodiment, or an embodiment combining software and hardware aspects. The systems and methods of use described herein can be performed using any type of computing device, such as a computer that includes a processor or any combination of computing devices where each device performs at least part of the process or method.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device. Communication between devices or components of a system can include both wired and wireless (e.g., RF, optical, or infrared) communications.

While the invention has been described in connection with various embodiments, it will be understood that the invention is capable of further modifications. This application is intended to cover any variations, uses, or adaptations of the invention following, in general, the principles of the invention and including such departures from the present disclosure as are within the known and customary practice within the art to which the invention pertains.

What is claimed is:

1. A method for automatic calibration, comprising:
performing an initial calibration of a catheter, based on internal catheter reflections that are stable in depth and consistent in intensity throughout the 360 degree rotation of the catheter, for a calibration position, the calibration including:
averaging an OCT image frame to selectively enhance high intensity features;
comparing a value of the image features to a pre-calibrated value; and
shifting the OCT image based on the comparison;
monitoring the internal catheter reflections of the calibration position;
determining if the calibration position needs updating on an image frame; and
updating the calibration position on a frame-by-frame basis.

2. The method of claim 1, wherein the image frame is an A-scan.

3. The method of claim 1, wherein the image frame includes a set of image frames.

* * * * *